US010682363B2

(12) United States Patent
Rathmacher et al.

(10) Patent No.: US 10,682,363 B2
(45) Date of Patent: *Jun. 16, 2020

(54) NUTRITIONAL INTERVENTION FOR IMPROVING MUSCULAR FUNCTION AND STRENGTH

(71) Applicant: Metabolic Technologies, Inc., Ames, IA (US)

(72) Inventors: John Rathmacher, Story City, IA (US); John Fuller, Jr., Zearing, IA (US); Shawn Baier, Polk City, IA (US); Steve Nissen, Ames, IA (US); Naji Abumrad, Nashville, TN (US)

(73) Assignee: Metabolic Technologies, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,375

(22) Filed: Dec. 21, 2018

(65) Prior Publication Data
US 2019/0209588 A1 Jul. 11, 2019

Related U.S. Application Data

(63) Continuation of application No. 15/648,911, filed on Jul. 13, 2017, now Pat. No. 10,201,551, which is a continuation of application No. 14/869,533, filed on Sep. 29, 2015, now Pat. No. 9,707,241, which is a continuation of application No. 14/861,728, filed on Sep. 22, 2015, now Pat. No. 9,539,224, which is a continuation-in-part of application No. 14/219,522, filed on Mar. 19, 2014, now Pat. No. 9,259,430, which is a continuation-in-part of application No. 12/634,507, filed on Dec. 9, 2009, now Pat. No. 8,815,280.

(60) Provisional application No. 61/121,065, filed on Dec. 9, 2008.

(51) Int. Cl.
| A61K 31/59 | (2006.01) |
| A61K 31/19 | (2006.01) |
| A23K 20/00 | (2016.01) |
| A23K 20/174 | (2016.01) |
| A23L 33/00 | (2016.01) |
| A23L 33/10 | (2016.01) |
| A23L 33/15 | (2016.01) |
| A23L 33/155 | (2016.01) |
| A23L 33/175 | (2016.01) |
| A61K 31/593 | (2006.01) |

(52) U.S. Cl.
CPC .............. *A61K 31/59* (2013.01); *A23K 20/00* (2016.05); *A23K 20/174* (2016.05); *A23L 33/10* (2016.08); *A23L 33/15* (2016.08); *A23L 33/155* (2016.08); *A23L 33/175* (2016.08); *A23L 33/30* (2016.08); *A61K 31/19* (2013.01); *A61K 31/593* (2013.01); *A23V 2002/00* (2013.01)

(58) Field of Classification Search
CPC ...... A61K 31/59; A61K 31/19; A61K 31/593; A23K 20/174; A23K 20/00; A23L 33/10; A23L 33/30; A23L 33/175; A23L 33/15; A23L 33/155; A23V 2002/00
See application file for complete search history.

(56) References Cited

U.S. PATENT DOCUMENTS

| 4,992,470 A | 2/1991 | Nissen |
| 5,028,440 A | 7/1991 | Nissen |
| 5,084,742 A | 2/1992 | Nissen |
| 5,348,979 A | 9/1994 | Nissen et al. |
| 5,360,613 A | 11/1994 | Nissen |
| 5,756,469 A | 5/1998 | Beale |
| 6,031,000 A | 2/2000 | Nissen et al. |
| 6,103,764 A | 8/2000 | Nissen |
| 6,291,525 B1 | 9/2001 | Nissen |
| 8,815,280 B2 * | 8/2014 | Rathmacher .......... A61K 31/19 424/439 |
| 9,259,430 B2 * | 2/2016 | Rathmacher .......... A61K 31/59 |
| 9,539,224 B2 * | 1/2017 | Rathmacher .......... A23L 33/10 |
| 9,707,241 B2 * | 7/2017 | Rathmacher .......... A23L 33/30 |
| 10,201,551 B2 * | 2/2019 | Rathmacher .......... A23L 33/30 |
| 2004/0071825 A1 | 4/2004 | Lockwood |
| 2005/0215640 A1 | 9/2005 | Baxter et al. |
| 2006/0003947 A1 | 1/2006 | Udell |
| 2007/0142469 A1 | 6/2007 | Thomas et al. |

FOREIGN PATENT DOCUMENTS

| WO | 2008024456 | 2/2008 |
| WO | 2012176026 | 12/2012 |

OTHER PUBLICATIONS

McCarty et al. Toward a Core Nutraceutical Program for Cancer Management, Integrative Cancer Therapies 2006, 150-171.*
Adamson et al., "The significance of certain carboxylic acids as intermediates in the biosynthesis of cholesterol.", "Biochim. Biophys Acta", Jan. 1, 1957, pp. 472-479., vol. 23.
Advertisement, "Delivering High Levels of HMB glutamine and lactoterrin", "High Performance Series", , Publisher: Met RX.
Associated Press, "Disfiguring Fat Adds to Aids Misery", Jan. 1, 1998, Publisher: Associated Press.
Bachhawat et al., "The enzymatic cleavage of beta-hydroxy-beta-methylglutaryl coenzyme a to aceto-acetate and acetyl coenzyme", "A. J. Biol. Chem", Jan. 1, 1955, pp. 727-736, vol. 216.

(Continued)

*Primary Examiner* — Blessing M Fubara
(74) *Attorney, Agent, or Firm* — Davis, Brown, Koehn, Shors & Roberts, P.C.; Emily E. Harris

(57) ABSTRACT

The present invention provides a composition comprising HMB and Vitamin D. Methods of administering HMB and Vitamin D to an animal are also described. Vitamin D and HMB are administered to increase muscle mass, strength, and functionality. The combination of Vitamin D and HMB together has a synergistic effect, which results in a surprising and unexpected level of improvement in muscle mass, strength and functionality.

19 Claims, 8 Drawing Sheets

(56) References Cited

OTHER PUBLICATIONS

Baier et al., "Year-long changes in lean body mass in elderly men and women supplemented with a nutritional cocktail of beta-hydroxy-beta-methylbutyrate (HMB), arginine, and lysine", "JPEN", Jan. 1, 2009, pp. 71-82, vol. 33.

Barbul, "Arginine: Biochemistry, Physiology, and Therapeutic Implications", "Journal of Parenteral and Enteral Nutrition", Jan. 1, 1986, vol. 10, No. 2, Publisher: American Society for Parenteral and En. Nutrition.

Birge et al., "25-hydroxycholecalciferol stimulation of muscle metabolism.", Jan. 1, 1975, pp. 1100-1107, vol. 56, Publisher: J. Clin. Invest.

Birge et al., "25-hydroxycholecalciferol stimulation of muscle metabolism", "J. Clin. Invest", Jan. 1, 1975, pp. 1100-1107, vol. 56.

Bischoff et al., "Effects of vitamin 0 and calcium supplementation on falls: a randomized controlled trial.", Jan. 1, 2003, pp. 343-351, vol. 18, Publisher: J. Bone Miner. Res.

Bischoff et al., "Estimation of optimal serum concentrations of 25-hydroxyvitamin 0 for multiple health outcomes.", Jan. 1, 2006, pp. 18-28, vol. 84, Publisher: Am. J. Clin. Nutr.

Bischoff et al., "In situ detection of 1, 25-dihydroxyvitamin 03 receptor in human skeletal muscle tissue", "Histochem.", Jan. 1, 2001, pp. 19-24, vol. 33.

Bischoff-Ferrari, H. A., Borchers, M., Gudat, F., Durmuller, U., Stahelin, H. B. & Dick, W., "Vitamin D receptor expression in human muscle tissue decreases with age.", "J. Bone Miner. Res.", Jan. 1, 2004, pp. 265-269, vol. 19.

Bloch et al., "Utilization of branched chain acids in cholesterol synthesis", "J. Biol. Chem", Jan. 1, 1954, pp. 687-699, vol. 211.

Boland et al., "Avian muscle cells as targets for the secosteroid hormone 1,25-dihydroxy-vitamin 03", Jan. 1, 1995, pp. 1-8, vol. 114, Publisher: Mol. Cell Endocrinol.

Boland et al., "nongenomic stimulation of tyrosine phosphorylation cascades by 1,25(OH)(2)D(3) by VDR-dependent and -independent mechanisms in muscle cells", "Steroids", Jan. 1, 2002, pp. 477-482, vol. 67.

Boland et al., "Presence of a 1,25-dihydroxy-vitamin 03 receptor in chick skeletal muscle myoblasts.", Jan. 1, 1985, pp. 305-311, vol. 128, Publisher: Biochem. Biophys. Res. Commun.

Boland, "Role of vitamin 0 in skeletal muscle function", Jan. 1, 1986, pp. 434-448, vol. 7, Publisher: Endocr. Rev.

Burne et al., "Behavioural characterization of vitamin 0 receptor knockout mice.", "Behav. Brain Res.", Jan. 1, 2005, pp. 299-308, vol. 157.

Capiati et al., "1,25(OH)2-vitamin 03 induces translocation of the vitamin 0 receptor (VDR) to the plasma membrane in skeletal muscle cells", Jan. 1, 2002, pp. 128-135, vol. 86, Publisher: J. Cell Biochem.

Clark et al., "Effect of an amino acid mixtrue containing HMB in HIV related wasting", "12th World AIDS Conference", Jun. 1, 1998, Published in: Geneva.

Clark et al., "Nutritional treatment for acquired immunodeficiency virus-associated wasting using beta-hydroxy-beta-methylbutyrate, glutamine and arginine: A randomized, double-blind, placebo-controlled study", "JPEN J Parenter Enteral Nutr", Jan. 1, 2000, pp. 133-139, vol. 24, No. 3.

Coon, "Enzymatic synthesis of branched chain acids from amino acids.", "Fed. Proc", Jan. 1, 1955, pp. 762-764, vol. 14.

Cornet et al., "1,25-Dihydroxyvitamin D3 regulates the expression of VDR and NGF gene in Schwann cells in vitro", "J Neurosci. Res", Jan. 1, 1998, pp. 742-746, vol. 53.

Costa et al., "1,25-dihydroxyvitamin D3 receptors and hormonal responses in cloned human skeletal muscle cells.", "Endocrinology", Jan. 1, 1986, pp. 2214-2220, vol. 119.

Daly et al., "Enteral nutrition with supplemental arginine RNA and omega 3 fatty acids in patients after operation: immunologic metabolic and clinical outcome", "Surgery", Jul. 1, 1992, pp. 56-67, vol. 11, No. 1, Publisher: PubMed.

Deboland, "In vitro cellular muscle calcium metabolism. Characterization of effects of 1,25-dihydroxy-vitamin 03 and 25-hydroxy-vitamin 03.", "Z. Naturforsch", Jan. 1, 1985, pp. 102-108, vol. 40.

Deluca, "The vitamin 0 story: a collaborative effort of basic science and clinical medicine", "FASEB", Jan. 1, 1988, pp. 224-236.

Deluca, "The vitamin D story: a collaborative effort of basic science and clinical medicine.", "FASEB", Jan. 1, 1988, pp. 224-236, vol. 2.

Eley et al., "Attenuation of depression of muscle protein synthesis induced bylipopolysaccharide, tumor necrosis factor and angiotensin II by beta-hydroxy-beta-methylbutyrate", "Am. J. Physiol D", Jan. 1, 2008, pp. E1409-E1416., vol. 295.

Eley et al., "Mechanism of Attenuation of Muscle Protein Degradation Induced by Tumor Necrosis Factor Alpha and Angiotensin II by beta-Hydroxy-beta-methylbutyrate", "Am J Physiol Endocrinol", Oct. 7, 2008, vol. 295.

Eley et al., "Signaling pathways initiated by b-hydroxy-b-methylbutyrate to attenuate the depression of protein synthesis in skeletal muscle in response to cachectic stimuli", "Am J Physiol Endocrinol Metab", Jul. 3, 2007, pp. E923-E931, vol. 293.

Eubanks et al., "Reversal of cancer-related wasting using oral supplementation with a combination of beta-hydroxy-beta-methylbutyrate, arginine, and glutamine.", "Am. J. Surg", Jan. 1, 2002, pp. 471-479, vol. 183.

Freedman, "Transcriptional targets of the vitamin 03 receptor-mediating cell cycle arrest and differentiation", "J. Nutr.", Jan. 1, 1999, pp. 581S-586S, vol. 129.

Frexes-Steed, "Role of insulin and branched-chain amino acids in regulating protein metabolism during fasting.", "Endocrinol. Metab", Jan. 1, 1990, pp. E907-E917, vol. 258, Publisher: Am. J. Physiol.

Fuller, J. C., Jr., Nissen, S. L. & Huiatt, T. W., "Use of 180-labelled leucine and phenylalanine to measure protein turnover in muscle cell cultures and possible futile cycling during aminoacylation.", Jan. 1, 1993, pp. 427-433, vol. 294, Publisher: Biochem.J.

Gallagher et al., "beta-Hydroxy-beta-methylbutyrate ingestion, Part I: Effects on strength and fat free mass.", "Med Sci Sports Exerc", Jan. 1, 2000, pp. 2109-2115, vol. 32, No. 12.

Gallagher et al., "beta-Hydroxy-beta-methylbutyrate ingestion, Part II: Effects on hematology, hepatic, and renal function.", "Med Sci Sports Exerc", Jan. 1, 2000, pp. 2116-2119, vol. 32, No. 12.

Gey et al., "The influence of isoperenic C5 and C6 compounds upon the acetate incorporation into cholesterol.", "Helvetica Chim. Acta", Jan. 1, 1957, pp. 2354-2368, vol. 40.

Gey et al., "Influence of iosoprenoid C5 and C6 compounds on the incorporation of acetate in cholesterol.", "Helvetica Chim. Acta", Jan. 1, 1957, pp. 2354-2368, vol. 40.

Gniadecki, R., Gajkowska, B. & Hansen, M., "1,25-dihydroxyvitamin D3 stimulates the assembly of adherens junctions in keratinocytes: involvement of protein kinase", "Endocrinology", Jan. 1, 1997, pp. 2241-2248, vol. 138.

Haddad et al., "25-Hydroxycholecalciferol: specific binding by rachitic tissue extracts", Jan. 1, 1971, pp. 829-834, vol. 45, Publisher: Biochem. Biophys Res Commun.

Haddad et al., "Widespread, specific binding of 25-hydroxycholecalciferol in rat tissues.", Jan. 1, 1975, pp. 299-303, vol. 250, Publisher: J Biol Chem.

Hammarqvist et al., "Glutamine in surgical nutrition and metabolism", "Amino Acids in Critical Care and Cancer", Jan. 1, 1994, pp. 27-44, Publisher: RG Landes Co.

Harper et al., "Effects of ingestion of disproportionate amounts of amino acids", "Physiol. Rev", Jan. 1, 1970, pp. 428-558, vol. 53.

Heaney et al., "Calcium absorption varies within the reference range for serum 25-hydroxyvitamin D", "J. Am. Coil. Nutr", Jan. 1, 2003, pp. 142-146, vol. 22.

Heaney, "Vitamin D in Health and Disease", "Clin. J. Am. Soc. Nephrol", Jan. 1, 2008, pp. 1535-1541, vol. 3.

Heaney, "Vitamin D endocrine physiology", "J. Bone Miner. Res", Jan. 1, 2007, pp. V25-V27., vol. 2.

Heislein et al., "A strength training program for postmenopausal women: a pilot study", "Arch. Phys. Med. Rehabil", Jan. 1, 1994, pp. 198-204, vol. 75.

(56) References Cited

OTHER PUBLICATIONS

Holick et al., "[Hormonal and metabolic causes of muscular weakness and the increased risk of fractures in elderly people", "Ned. Tijdschr", Jan. 1, 2005, pp. 1033-1037, vol. 149.
Met Rx, "Met-Rx High performance series discover a whole new training regimen", , Publisher: Met Rx.
Advertisement, "Twinlab—GrowthFuel", , Publisher: Twin Lab.
Advertisement, "Twinlab anti-catabolic HMB fuel plus", , Publisher: Twin Lab.
Vazquez et al., "1 alpha,25-(OH)2-vitamin D3 stimulates the adenylyl cyclasepathway in muscle cells by a GTP-dependent mechanism which presumably involves phosphorylation of G alpha i.", "Biochem. Biophys. Res. Commun.", Jan. 1, 1997, pp. 125-128, vol. 234.
Vieth et al., "The urgent need to recommend an intake of vitamin 0 that is effective", Jan. 1, 2007, pp. 649-650, vol. 85, Publisher: Am. J. D Clin. Nutr.
Vukovich et al., "Body composition in 70-year old adults responds to dietary beta-hydroxy-beta-methylbutyrate (HMB) similar to that of young adults", "J. Nutr", Jan. 1, 2001, pp. 2049-2052, vol. 131, No. 7.
Advertisement, "We know your sports nutrition customers", , Publisher: Twin Lab.
Wicherts et al., "Vitamin o status predicts physical performance and its decline in older persons", Jan. 1, 2007, pp. 2058-2065, vol. 92, Publisher: J. Clin. Endocrinol. Metab.
Wu et al., "p38 and extracellular signal-regulated kinases regulate the myogenic program at multiple steps.", "Mol. Cell Biol", Jan. 1, 2000, pp. 3951-3964, vol. 20.
Xu, H., McCann, M., Zhang, Z., Posner, G. H., Bingham, V., El-Tanani, M. & Campbell, F. C., "Vitamin D receptor modulates the neoplastic phenotype through antagonistic growth regulatory signals.", "Mol. Carcinog.", Jan. 1, 2009, pp. 758-772, vol. 48.
Zabin et al., "The utilization of butyric acid for the synthesis of cholesterol and fatty acids", "J. Biol. Chem", Jan. 1, 1951, pp. 261-266, vol. 192.
Zanello et al., "cDNA sequence identity of a vitamin D-dependent calcium binding protein in the chick to calbindin D-9K.", "Endocrinology", Jan. 1, 1995, pp. 2784-2787, vol. 136.
Zehnder, D., Bland, R., Williams, M. C., McNinch, R. W., Howie, A. J., Stewart, P. M. & Hewison, M., "Extrarenal expression of 25-hydroxyvitamin d(3)-1 alpha-hydroxylase", "J. Clin. Endocrinol. Metab", Jan. 1, 2001, pp. 888-894, vol. 86.
Zion et al., "home-based resistance-training program using elastic bands for elderly patients with orthostatic hypotension.", "Clin. Auton. Res", Jan. 1, 2003, pp. 286-292, vol. 13.
Holick, "Vitamin D deficiency", "N. Engl. J. Med", Jan. 1, 2007, pp. 266-281, vol. 357.
Advertisement, "HPS Met-RX", "High Performance Series", , Publisher: Met Rx.
Isler et al., "Biosynthesis of cholesterol from beta,t-dihydroxy-beta-methylvaleric acid", "Helvetica Chim. Acta", Jan. 1, 1957, pp. 2369-2373, vol. 40.
Jones, G., "Expanding role for vitamin D in chronic kidney disease: importance of blood 25-0H-D levels andextra-renal 1 alpha-hydroxylase in the classical and nonclassical actions of 1alpha,25-dihydroxyvitamin D", "Semin. Dial", Jan. 1, 2007, pp. 316-324, vol. 20.
Jowko et al., "Creatine and beta-hydroxy-beta-methylbutyrate (HMB) additively increase lean body mass and muscle strength during a weight-training program", "Nutrition", 2001, pp. 558-566, vol. 17.
Knitter et al., "Effects of beta-hyroxy-methylbutyrate on muscle damage following a prolonged run", "J Appl. Physiol", Jan. 1, 2000, pp. 1340-1344, vol. 89, No. 4.
Krebs, H. A. & Lund, P., "Aspects of the regulation of the metabolism of branched-chain amino acids.", "Advan. Enzyme Regul.", Jan. 1, 1977, pp. 375-394, vol. 15.
Krebs et al., "Moderate exercise improves gait stability in disabled elders.", "Arch. Phys. Med. Rehabil.", Jan. 1, 1998, pp. 1489-1495, vol. 79.

Kreider et al., "Effects of calcium beta-hydroxy-beta-methylbutyrate (HMB) supplementation during resistance-training on markers of catabolism, body composition and strength.", "Int J Sports Med", Jan. 1, 1999, pp. 503-509, vol. 20.
McAllan et al., "The efficiency of microbial protein synthesis in the rumen and the degradability of feed nitrogen between the mouth and abomasum in steers given different diets", "Br. J. Nutr", Jan. 1, 1984, pp. 77-83, vol. 51.
McCarty et al.., "Toward a Core Nutraceutical Program for Cancer Management", Jan. 1, 2006, pp. 150-171, vol. 5, No. 2.
McCarty et al., "Toward a Core Nutraceutical Program for Cancer Management", "Integrative Cancer Therapies", 2006, pp. 150-171, vol. 5, No. 2.
Menconi, M., Gonnella, P., Petkova, V., Lecker, S. & Hasselgren, P. O, "Dexamethasone and corticosterone induce similar, but not identical, muscle wasting responses in cultured L6 and C2C12 myotubes.", Jan. 1, 2008, pp. 353-364, vol. 105, Publisher: J Cell Biochem.
Advertisement, "Met-RX engineered nutrition", "High Performance Series", , Publisher: Met RX.
Advertisement, "Take your nutrition to new levels of performance", , Publisher: Met RX.
Advertisement, "Met-RX engineered nutrition Anabolic Drive", , Publisher: Met RX.
Morelli et al., "1,25(OH)2-vitamin D3 stimulation ofphospholipases C and D in muscle cells involves extracellular calcium and a pertussis-sensitive G protein.", "Mol. Cell Endocrinol.", Jan. 1, 1996, pp. 207-211, vol. 122.
Global Reach, "MTI-AIDS NCMC001—Study Outline", , Publisher: Global Reach.
Nemere et al., "Identification of a specific binding protein for 1 alpha,25-dihydroxyvitamin 03 in basal-lateral membranes of chick intestinal epithelium andrelationship to transcaltachia", Jan. 1, 1994, pp. 23750-23756, vol. 269, Publisher: J. Biol. Chem.
Neu et al., "Glutamine nutrition and metabolism: where do we go from here?", "FASEB Journal", Jun. 1, 1996, pp. 829-837, vol. 10.
Nieuwenhuijzen Kruseman, A. C., Van Der Klauv, M. M. & Pijpers, E., "Hormonal and metabolic causes of muscular weakness and the increased risk of fractures in elderly people", Jan. 1, 2005, pp. 1033-1037, vol. 149, Publisher: Ned. Tijdschr. Geneeskd.
Nissen et al., "Analysis of beta-hydroxy-beta-methyl butyrate in plasma by gas chromatography and mass spectrometry.", "Anal. Biochem", Jan. 1, 1990, pp. 17-19, vol. 188.
Nissen et al., "beta-Hydroxy-beta-methylbutyrate (HMB) supplementation in humans is safe and may decrease cardiovascular risk factors", "J Nutr", Jan. 1, 2000, pp. 1937-1945, vol. 130.
Nissen, "Effect of dietary supplements on lean mass and strength gains with resistance exercise: a meta-analysis", "J Appl. Physiol", Jan. 1, 2003, pp. 651-659, vol. 94.
Nissen et al., "The effect of the leucine metabolite beta-hydroxy beta-methylbutyrate on muscle metabolism during resistance-excersise training", "J. Appl. Physiol", Jan. 1, 1996, pp. 2095-2104, vol. 81, No. 5.
Nissen et al., "Nutritional role of the leucine metabolite beta-hydroxy-beta-methylbutyrate (HMB).", "J. Nutr. Biochem", Jan. 1, 1997, pp. 300-311, vol. 8.
Ostaszewski et al., "The leucine metabolite 3-hydroxy-3-methylbutyrate (HMB) modifies protein turnover in muscles of the laboratory rats and domestic chicken in vitro.", "J. Anim. Physiol. Anim. Nutr.", Jan. 1, 2000, pp. 1-8, vol. 84.
Panton et al., "Nutritional supplementation of the leucine metabolite beta-hydroxy beta-methylbutyrate (HMB) during resistance training", "Nutr.", Jan. 1, 2000, pp. 734-739, vol. 16, No. 9.
Pichard et al., "Randomized double-bline controlled study of 6 months of oral nutritional supplementation with arginine and omega 3 fattyacids in HIV infected patients", "AIDS", Jan. 1, 1998, pp. 53-63, vol. 12, No. 1, Publisher: PubMed.
Plaut et al., "Enzymatic incorporation of C14-bicarbonate into acetoacetate in the presence of various substrates.", "J. Biol. Chem. ", Jan. 1, 1951, pp. 435-445, vol. 192.
Rabinowitz et al., "Branched chain acids in the biosynthesis of squalene and cholesterol.", "Fed. Proc", Jan. 1, 1955, pp. 760-761, vol. 14.

(56) References Cited

OTHER PUBLICATIONS

Rathmacher et al., "The effect of the leucine metabolite beta-hydroxy-beta-methylbutyrate on lean body mass and muscle strength during prolonged bed res!.", "FASEB", Jan. 1, 2001, pp. A909, vol. 13.

Rathmacher et al., "Supplementation with a combination of beta-hydroxy-beta-methylbutyrate (HMB), arginine, and glutamine is safe and could improve hematological parameters", "JPEN J Parenter Enteral Nutr", Jan. 1, 2004, pp. 65-75, vol. 28.

Robinson et al., "Enzymatic carbon dioxide fixation by senecioyl coenzyme", "A Fed. Proc", Jan. 1, 1954, p. 281, vol. 13.

Rogers, "Effects of dumbbell and elastic band training on physical function in older inner-city African-American women", "Women Health", Jan. 1, 2002, pp. 33-41, vol. 36.

Rudney et al., "Biosynthesis of branched chain acids", "Fed. Proc.", Sep. 1, 1955, pp. 757-759.

Rudney, "The synthesis of beta-hydroxy-beta-methylglutaric acid in rat liver homogenates", "J. Am. Chem. Soc", Jan. 1, 1954, p. 2595 vol. 76.

Sanchez et al., "1,25-Dihydroxyvitamin D3 administration to 6-hydroxydopamine-lesioned rats increases glial cell line-derived neurotrophic factor and partially restores tyrosine hydroxylase expression in substantia nigra and striatum", "J Neurosci. Res", Jan. 1, 2009, pp. 723-732., vol. 87.

Sato et al., "low-dose vitamin D prevents muscular atrophy and reduces falls and hip fractures in women after stroke: a randomized controlled trial.", Jan. 1, 2005, pp. 187-192, vol. 20, Publisher: Cerebrovasc. Dis.

Selles et al., "Rapid stimulation of calcium uptake and protein phosphorylation in isolated cardiac muscle by 1,25-dihydroxyvitamin D3.", "Mol. Cell Endocrinol", Jan. 1, 1991, pp. 67-73, vol. 77.

Simpson et al., "Identification of 1,25-dihydroxyvitamin 03 receptors and activities in muscle", Jan. 1, 1985, pp. 8882-8891, vol. 260, Publisher: J. Biol. Chem.

Slater et al., "beta-hydroxy beta-methylbutyrate (HMB) supplementation does not affect changes in strength or body composition during resistancE D", "In!. J. Sport Nutr. Exerc. Metab", Jan. 1, 2001, pp. 384-396, vol. 11.

Smith et al., "Attenuation of proteasome-induced proteolysis in skeletal muscle by b-hydroxy-b-methylbutyrate in cancer-induced muscle loss", "Cancer Research", Jan. 1, 2005, pp. 277-283, vol. 65.

Smith et al., "Mechanism of the attenuation of proteolysis-inducing factor stimulated protein degradation in muscle by beta-hydroxy-beta-methylbutyrate", "Cancer Res", Jan. 1, 2004, pp. 8731-8735, vol. 64.

Snijder et al., "Vitamin 0 status in relation to one-year risk of recurrent falling in older men and women.", Jan. 1, 2006, pp. 2980-2985, vol. 91, Publisher: J. Clin. Endocrinol. Metab.

Somjen, D., Weisman, Y., Kohen, F., Gayer, B., Limor, R., Sharon, 0., Jaccard, N., Knoll, E. & Stern, N., "25-hydroxyvitamin D3-1alpha-hydroxylase is expressed in human vascular smooth muscle cells and is upregulated by D", Jan. 1, 2005, pp. 1666-1671, vol. 111, Publisher: Circulation.

Sousa et al., "Calcium b-hydroxy-b-methylbutyrate. Potential role as a phosphate binder in uremia", "Nephron", 1996, pp. 391-394, vol. 72, Publisher: Karger.

Suttmann et al., "Weight gain and increased concentrations of receptor proteins for tumor necrosis factor after patients with symptomatic HIV infections received fortified nutrition support", "J Am Diet Assoc", Jun. 1, 1996, pp. 565-569, vol. 6, No. 6, Publisher: PubMed.

Torosian, "Arginine in nutrition and surgery: current status and potential", "Amino Acids in Critical Care and Cancer", Jan. 1, 1994, pp. 45-52, Publisher: RG Landes Co.

\* cited by examiner

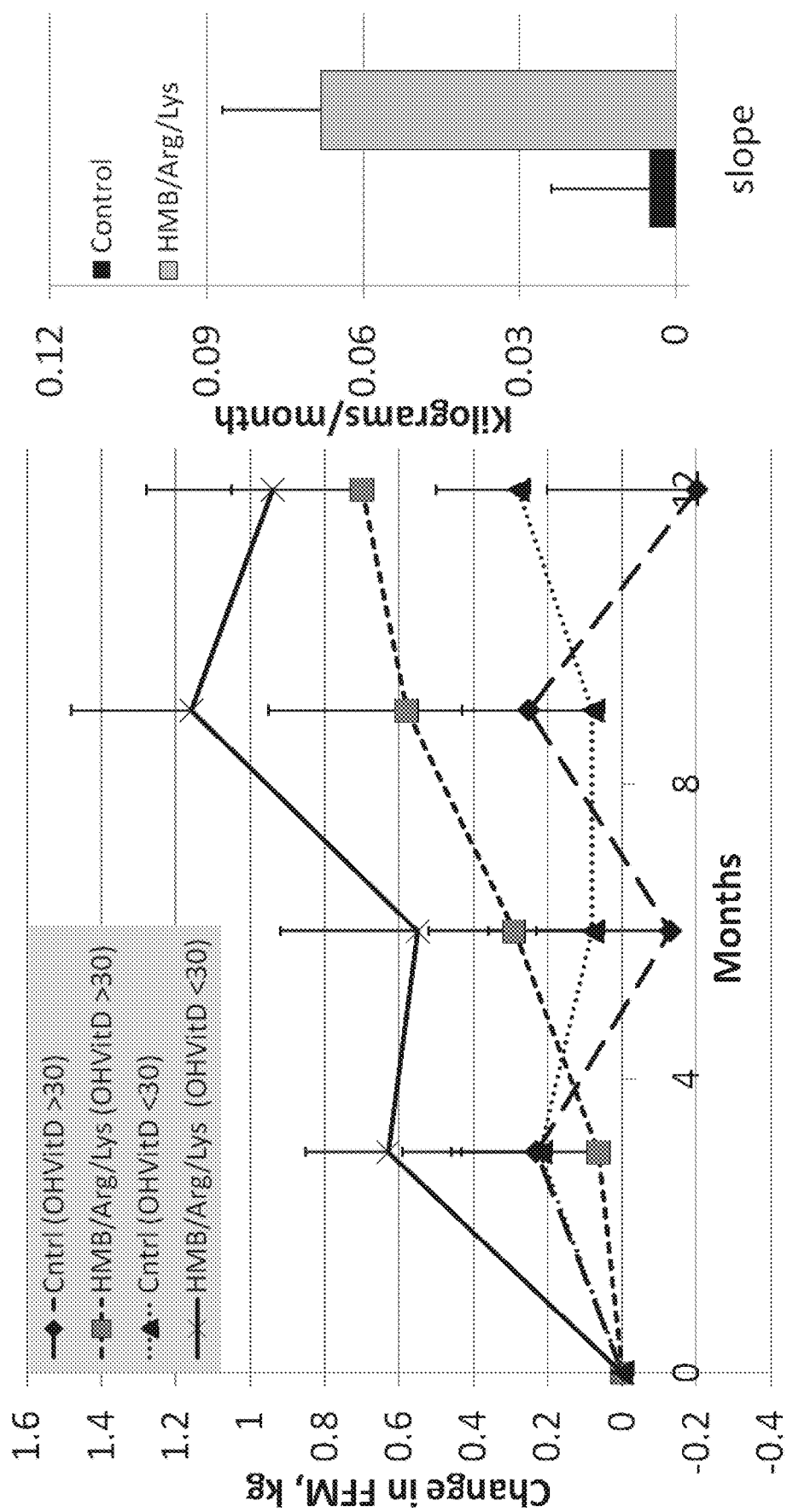
Figure 1a. Year-long changes in muscle mass separated by 25OH-VitD$_3$ status (line graph) and overall change per month (bar graph)

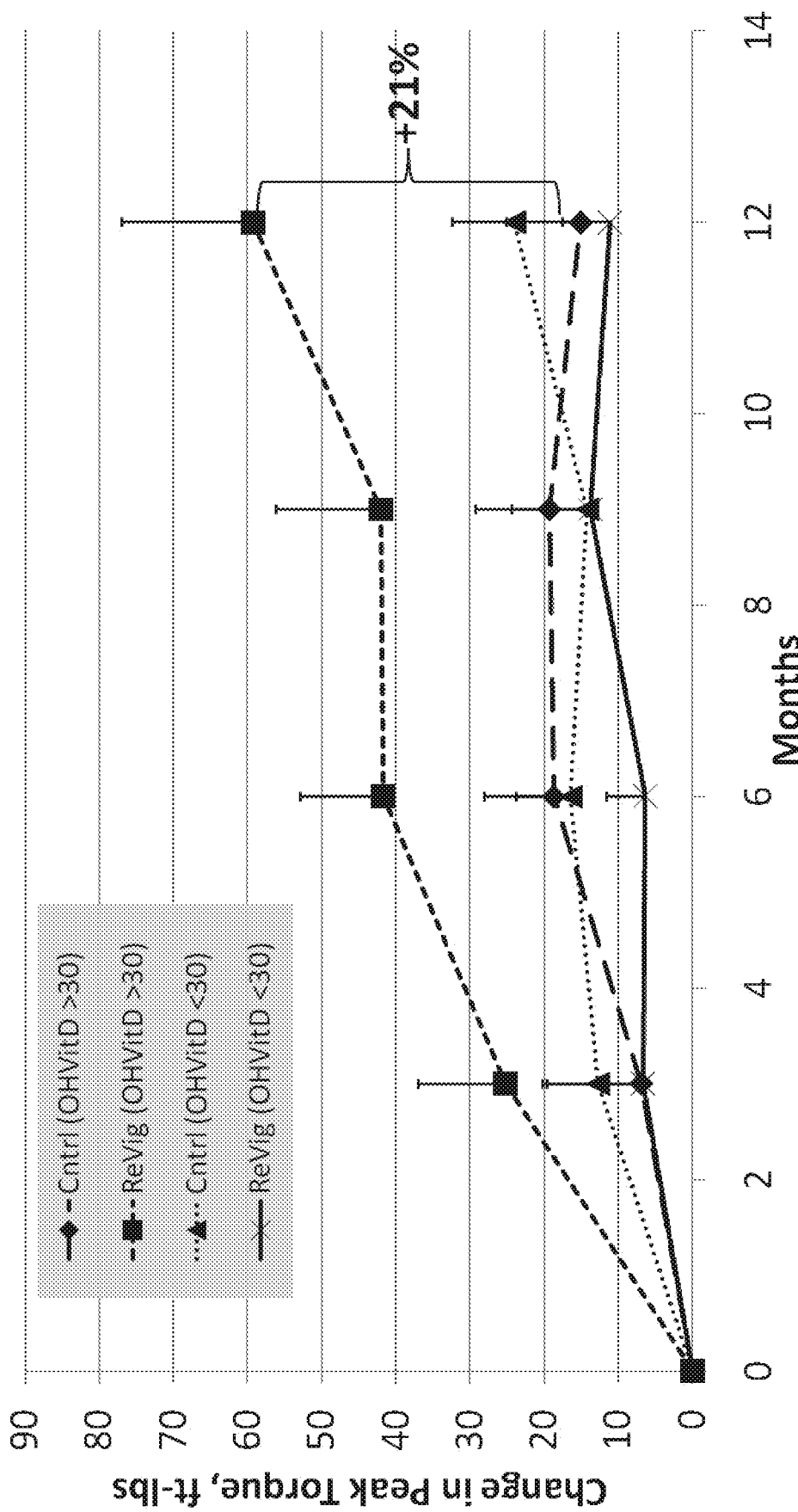
Figure 1b. Change in overall knee strength separated by 25OH-VitD$_3$ status

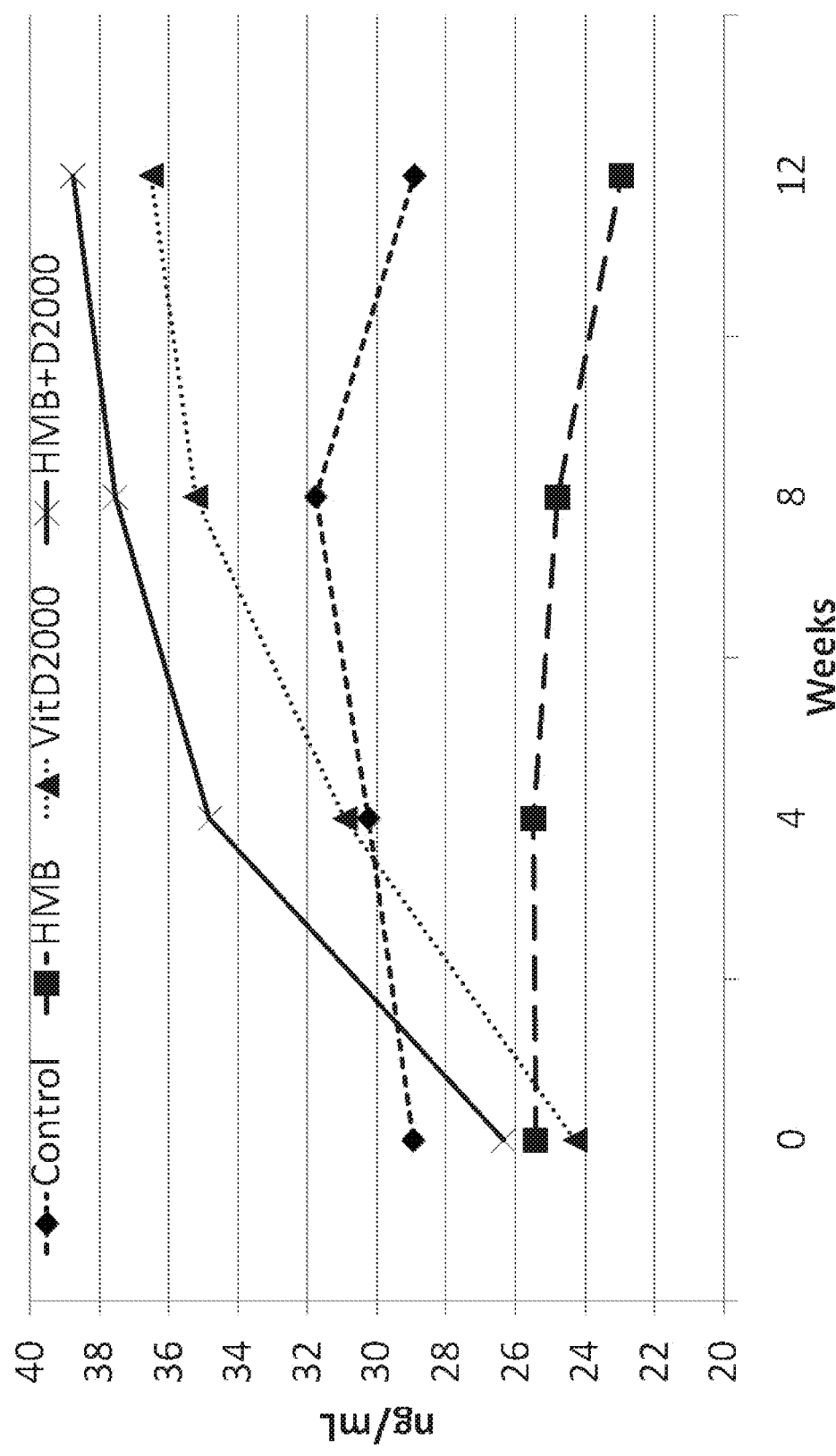

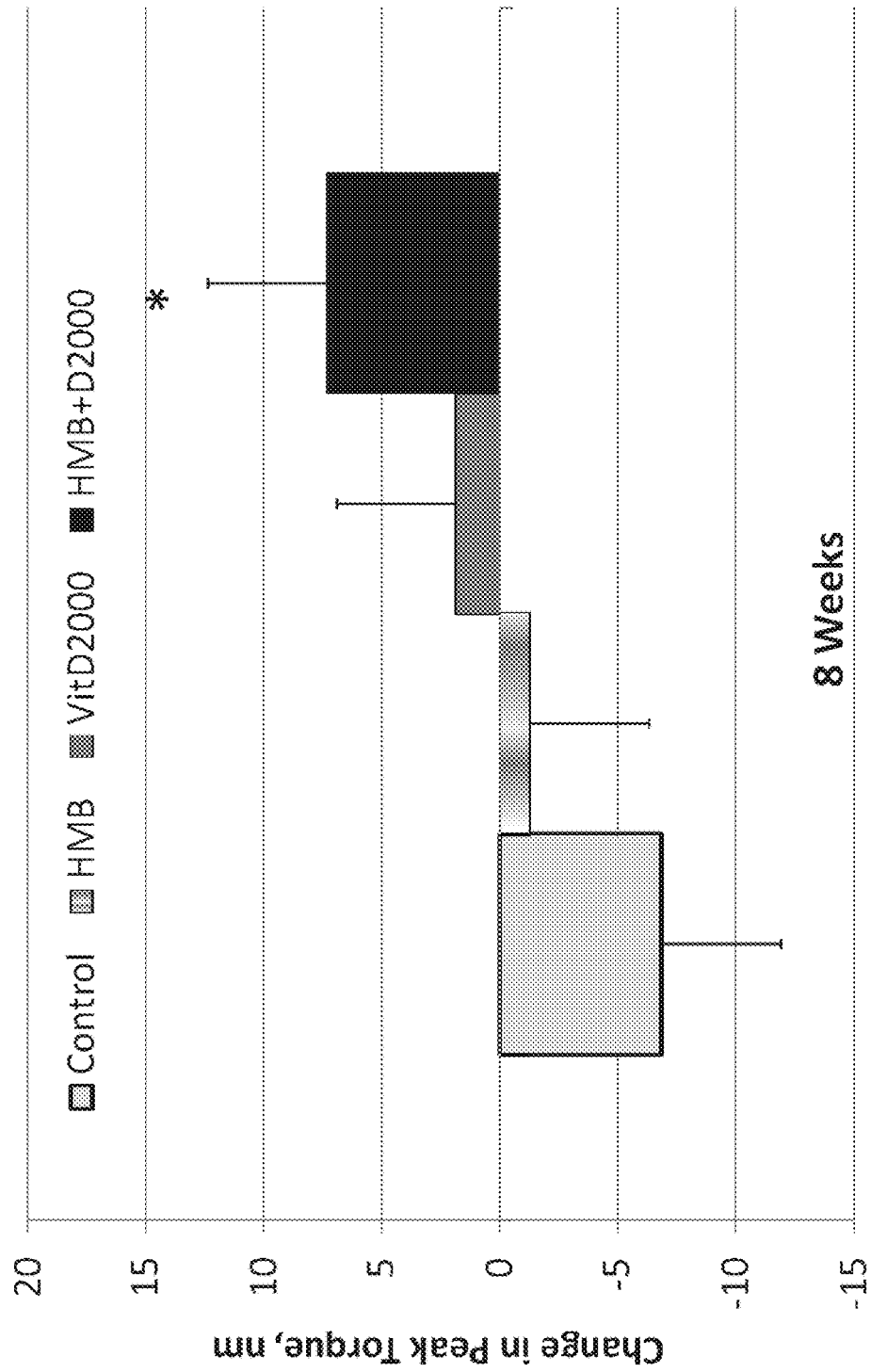

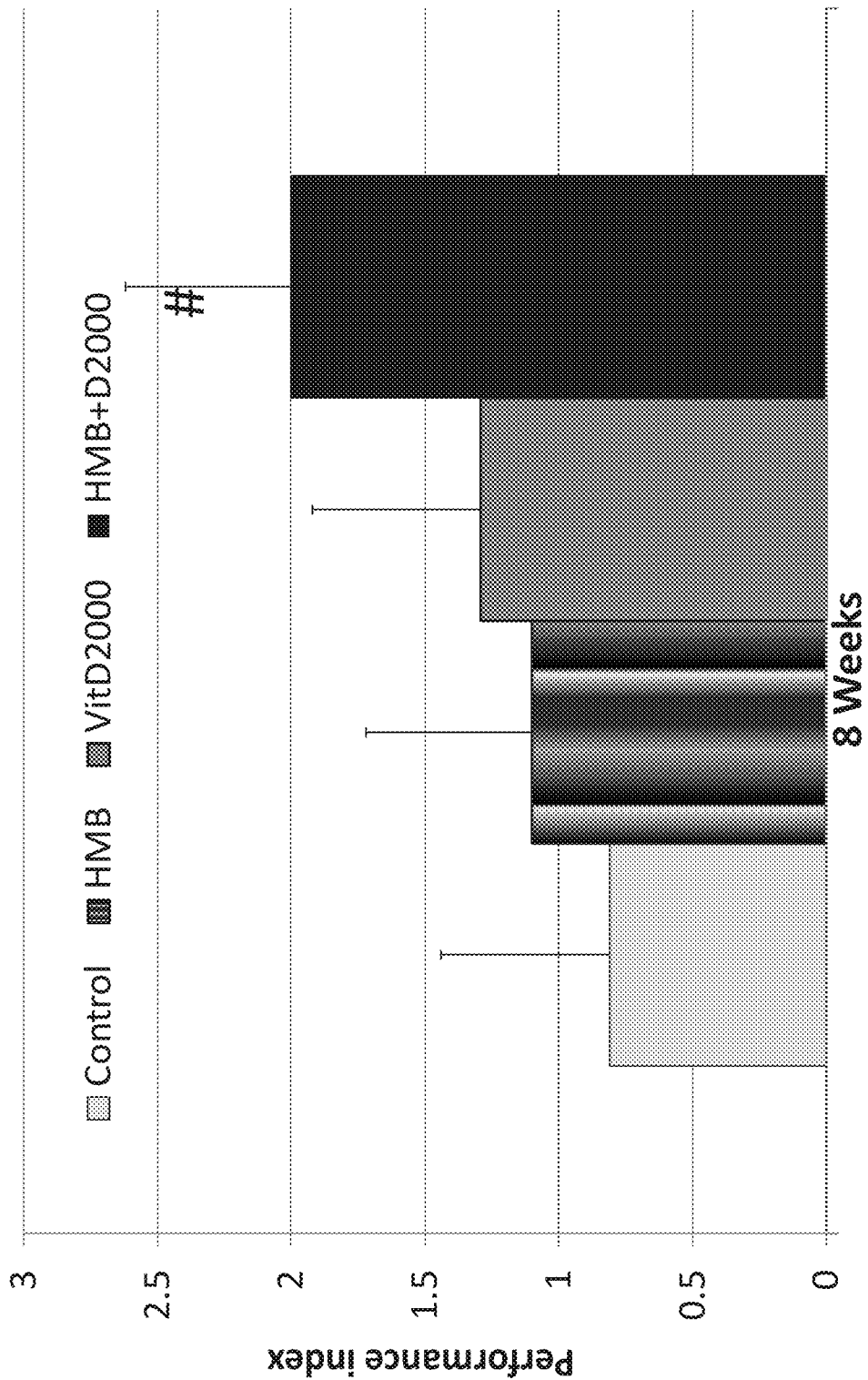

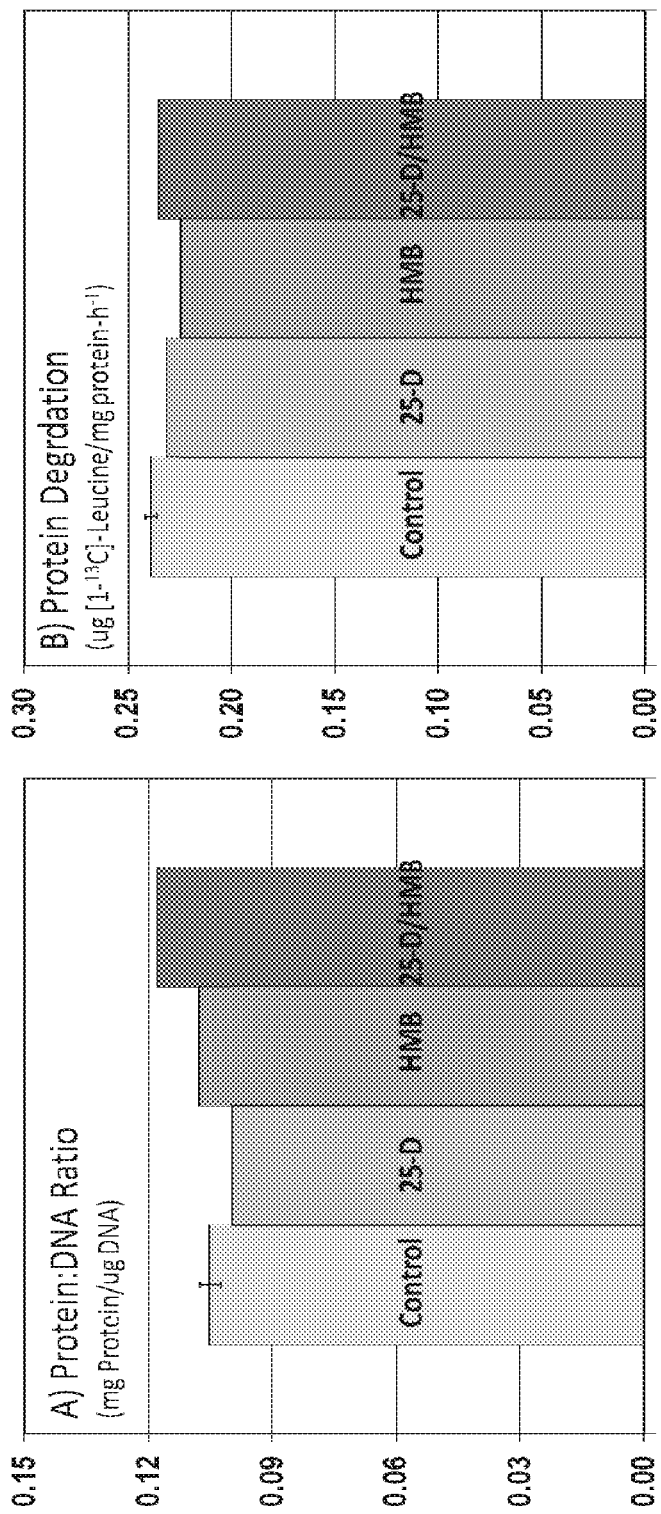
Figure 3. Protein:DNA ratio (A) and Protein degradation (B) in C2C12 cells treated with Control, 25OH-VitD$_3$ (200 ng/mL), HMB (200 μM as Ca(HMB)$_2$-H$_2$O), or the combination.

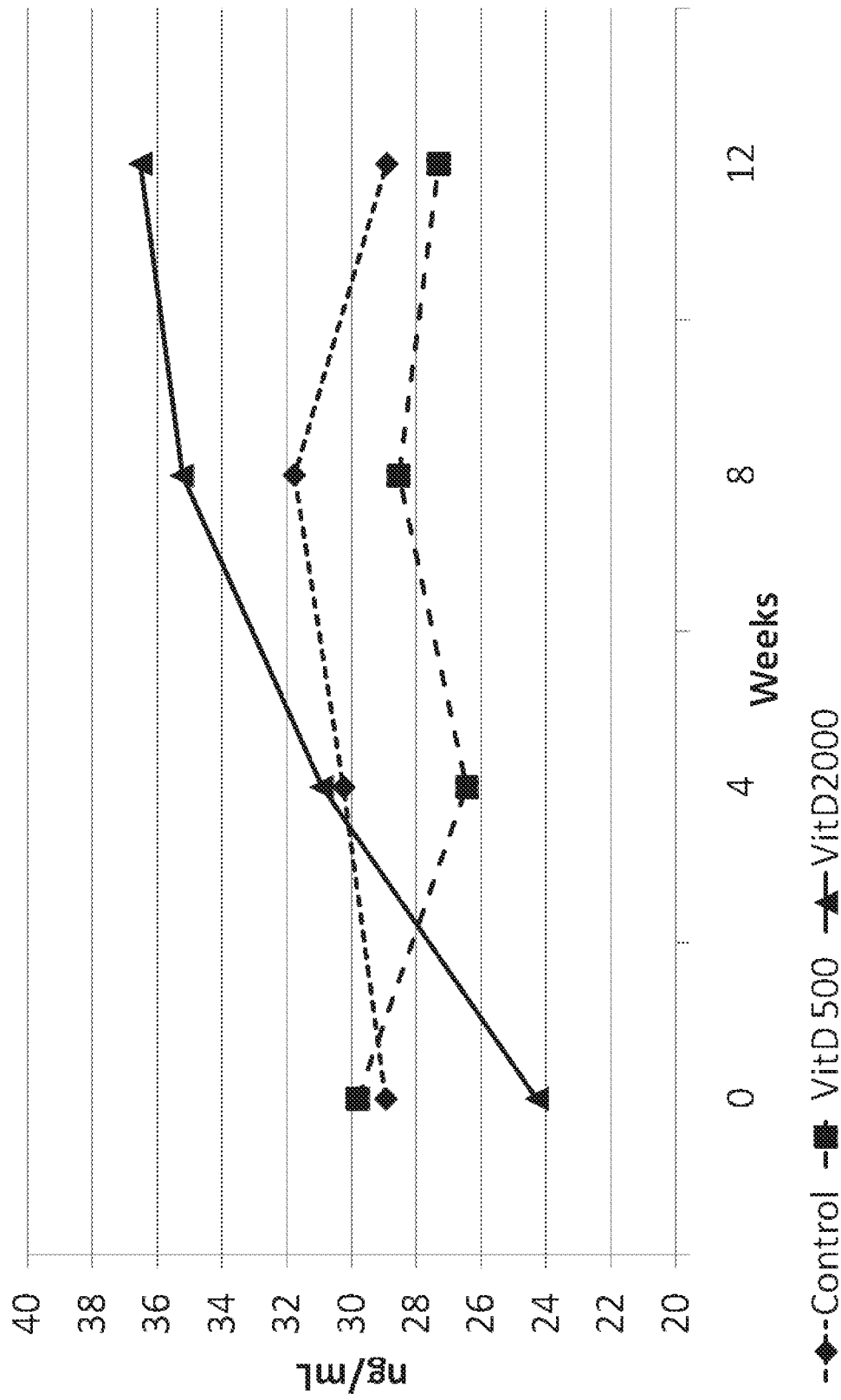

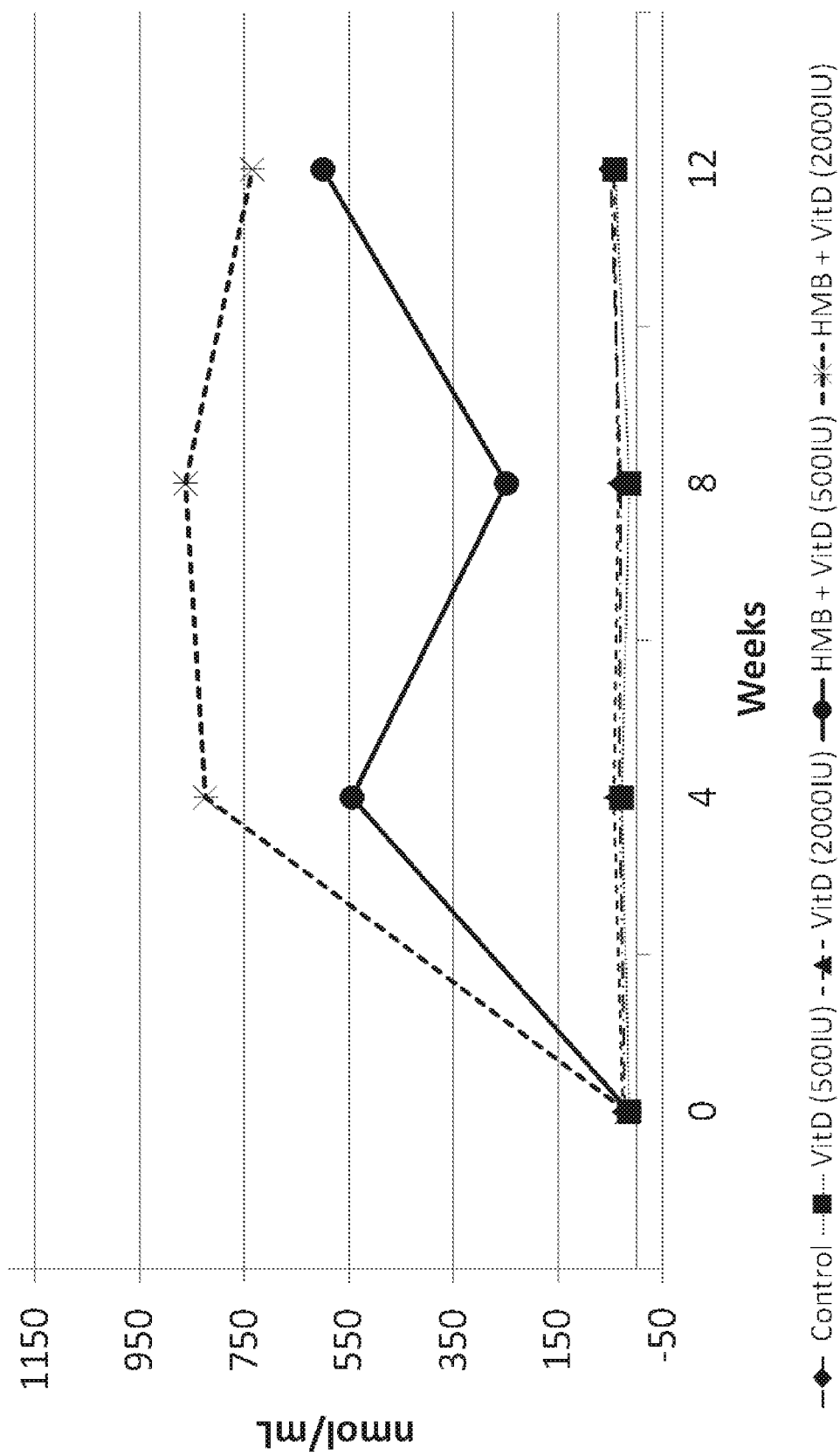

NUTRITIONAL INTERVENTION FOR IMPROVING MUSCULAR FUNCTION AND STRENGTH

This application is a continuation of U.S. patent application Ser. No. 15/648,911, filed Jul. 13, 2017, which is a continuation of U.S. patent application Ser. No. 14/869,533, filed Sep. 29, 2015, which is a continuation-in-part of U.S. patent application Ser. No. 14/861,728, filed Sep. 22, 2015, which is a continuation-in-part of U.S. patent application Ser. No. 14/219,522, filed Mar. 19, 2014, which is a continuation-in-part of U.S. patent application Ser. No. 12/634,507, filed Dec. 9, 2009, which claims the benefit of U.S. Provisional Application No. 61/121,065, filed Dec. 9, 2008, and herein incorporates U.S. Provisional Application No. 61/121,065 by reference.

BACKGROUND OF THE INVENTION

1. Field

The present invention relates to a composition comprising β-hydroxy-β-methylbutyrate (HMB) and Vitamin D, and methods of using a combination of HMB and Vitamin D to improve muscle mass, strength, or functionality.

2. Background

HMB

The only product of leucine metabolism is ketoisocaproate (KIC). A minor product of KIC metabolism is β-hydroxy-β-methylbutyrate (HMB). HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in animals. Also, in U.S. Pat. No. 4,992,470 (Nissen), HMB is described as effective in enhancing the immune response of mammals. U.S. Pat. No. 6,031,000 (Nissen et al.) describes use of HMB and at least one amino acid to treat disease-associated wasting.

It has previous been observed that HMB alone or in combination with other amino acids is an effective supplement for restoring muscle strength and function in young athletes. Further, it has been observed that HMB in combination with two amino acids, glutamine and lysine, is effective in increasing muscle mass in elderly persons.

HMB is an active metabolite of the amino acid leucine. The use of HMB to suppress proteolysis originates from the observations that leucine has protein-sparing characteristics (1-4). The essential amino acid leucine can either be used for protein synthesis or transaminated to the α-ketoacid (α-ketoisocaproate, KIC)(1, 3). In one pathway, KIC can be oxidized to HMB. Approximately 5% of leucine oxidation proceeds via the second pathway (5). HMB is superior to leucine in enhancing muscle mass and strength. The optimal effects of HMB can be achieved at 3.0 grams per day, or 0.38 g/kg of body weight per day, while those of leucine require over 30.0 grams per day (3).

Once produced or ingested, HMB appears to have two fates. The first fate is simple excretion in urine. After HMB is fed, urine concentrations increase, resulting in an approximate 20-50% loss of HMB to urine (4, 6). Another fate relates to the activation of HMB to HMB-CoA (7-16). Once converted to HMB-CoA, further metabolism may occur, either dehydration of HMB-CoA to MC-CoA, or a direct conversion of HMB-CoA to HMG-CoA (17), which provides substrates for intracellular cholesterol synthesis. Several studies have shown that HMB is incorporated into the cholesterol synthetic pathway (12, 16, 18-20) and could be a source for new cell membranes that are used for the regeneration of damaged cell membranes (3). Human studies have shown that muscle damage following intense exercise, measured by elevated plasma CPK (creatine phosphokinase), is reduced with HMB supplementation within the first 48 hrs. The protective effect of HMB lasts up to three weeks with continued daily use (21-23).

In vitro studies in isolated rat muscle show that HMB is a potent inhibitor of muscle proteolysis (24) especially during periods of stress. These findings have been confirmed in humans; for example, HMB inhibits muscle proteolysis in subjects engaging in resistance training (4). The results have been duplicated in many studies (25) (21-23, 26-28).

The molecular mechanisms by which HMB decreases protein breakdown and increases protein synthesis have recently been reported (29-31, 31-33). In mice bearing the MAC16 cachexia-inducing tumor, HMB attenuated protein degradation through the down-regulation of key activators of the ubiquitin-proteasome pathway (30). Furthermore, HMB attenuated proteolysis-inducing factor (PIF) activation and increased gene expression of the ubiquitin-proteasome pathway in murine myotubes, thereby reducing protein degradation (31). PIF inhibits protein synthesis in murine myotubes by 50% and HMB attenuates this depression in protein synthesis (29). Eley et al demonstrated that HMB increases protein synthesis by a number of mechanisms, including the down-regulation of eukaryotic initiation factor 2 (eIF2) phosphorylation through an effect on dsRNA-dependant protein kinase (PKR) and upregulation of the mammalian target of rapamycin/70-kDa ribosomal S6 kinase (mTOR/p70$^{S6k}$) pathway. The net result is increased phosphorylation of 4E-binding protein (4E-BP1) and an increase in the active eIF4G.eIF4E complex. Leucine shares many of these mechanisms with HMB, but HMB appears to be more potent in stimulating protein synthesis (29).

HMB can also increase protein synthesis by attenuating the common pathway that mediates the effects of other catabolic factors such as lipopolysaccharide (LPS), tumor necrosis factor-α/interferon-γ (TNF-α/IFN-γ), and angiotensin II (Ang II) (32, 33). HMB acts by attenuating the activation of caspases-3 and -8, and the subsequent attenuation of the activation of PKR and reactive oxygen species (ROS) formation via down-regulation of p38 mitogen activated protein kinase (p38MAPK). Increased ROS formation is known to induce protein degradation through the ubiquitin-proteasome pathway. HMB accomplishes this attenuation through the autophosphorylation PKR and the subsequent phosphorylation of eIF2α, and in part, through the activation of the mTOR pathway.

Numerous studies have shown an effective dose of HMB to be 3.0 grams per day as CaHMB (~38 mg/kg body weight-day$^{-1}$). This dosage increases muscle mass and strength gains associated with resistance training, while minimizing muscle damage associated with strenuous exercise (34) (4, 23, 26). HMB has been tested for safety, showing no side effects in healthy young or old adults (35-37). HMB in combination with L-arginine and L-glutamine has also been shown to be safe when supplemented to AIDS and cancer patients (38).

Studies in humans have also shown that dietary supplementation with 3 grams of CaHMB per day plus amino acids attenuates the loss of muscle mass in various conditions such as cancer and AIDS. (3, 4, 26, 34, 39, 40) A meta-analysis of supplements to increase lean mass and strength with weight training showed HMB to be one of only 2 dietary supplements that increase lean mass and strength with exercise (34). More recently it was shown that HMB and the amino acids arginine and lysine increased lean mass in a non-exercising, elderly population over a year-long study.

Vitamin D

Vitamin D has classically been associated with calcium and phosphorous metabolism and bone strength. Until recently, an adequate Vitamin D level has been defined using the Vitamin D deficiency disease rickets. While $1,25OH_2\text{-}VitD_3$ is the active metabolite of Vitamin D, a measure of Vitamin D status widely accepted is serum (blood) circulating 25OH-VitD3. A circulating blood level between 10 and 15 ng 25OH-VitD3/mL will cause rickets in young children and has been accepted as the deficiency level for Vitamin D. Vitamin D can be synthesized by humans with adequate sun exposure or can be obtained through the diet and through supplements to the diet. Many factors influence the amount and effectiveness of Vitamin D found in the body. These factors include dietary intake, sun exposure, Vitamin D receptor number (VDR), conversion rate from cholecalciferol to 25OH-VitD3 and finally the conversion of 25OH-VitD3 to $1,25OH_2\text{-}VitD_3$.

Most of the population in northern latitudes (most of the United States) do not produce Vitamin D in the winter regardless of sun exposure because the sun's ultraviolet B rays do not reach the earth during that time and therefore the only source of Vitamin D is dietary (42). As the 25 hydroxylation occurs in the liver and the 1 hydroxylation occurs primarily in the kidney, these two organs play a large role in determining the circulating levels of Vitamin D, and the functioning of these organs and thus Vitamin D status tends to decrease with age (42).

In a recent review, Holick details research showing that circulating levels of 25OH-VitD3 must reach as high as 30-40 ng/mL before parathyroid hormone (PTH) levels begin to plateau (43). Other researchers have found that increasing 25OH-VitD3 from 20 to 32 ng/mL increased intestinal calcium transport (44). Both of these criteria would point to a 25OH-VitD3 level of 30 ng/mL or greater being required for optimal regulation of calcium metabolism in the body. A recent review by Heaney describes the optimal level of 25OH-VitD3 to be 32 ng/mL or greater for optimal health which takes into account a number of aspects other than bone health and calcium metabolism (45). By these standards, from 40 to 100% of independent elderly men and women are Vitamin D deficient (43).

The 1-alpha, 25-Vitamin D hydroxylase in the kidney has been considered the primary source for synthesis of the circulating active metabolite of Vitamin D, $1,25OH_2\text{-}VitD_3$. The activity of this enzyme is regulated on a whole body level by parathyroid hormone (PTH). Regulating $1,25OH_2\text{-}VitD_3$ on a whole body level probably does not provide for optimal levels of the active vitamin for all body tissues at one time. Relatively recently tissue specific 1-alpha, 25-Vitamin D hydroxylases have been identified and are thought to mediate autocrine responses of Vitamin D at the tissue specific level (46, 47). Human vascular smooth muscle has 1-alpha, 25-Vitamin D hydroxylase activity with a Km of 25 ng/mL. This means that the enzyme is operating at one half maximal capacity at a 25OH-VitD3 concentration of 25 ng/mL (48). Therefore serum levels of >25 ng/mL may be necessary for optimal active Vitamin D for vascular smooth muscle cells.

Muscle strength declines with age and a recently characterized deficiency symptom of Vitamin D is skeletal muscle weakness (43). Deficiency of Vitamin D and its hormonal effect on muscle mass and strength (sarcopenia) has been described as a risk factor in falls and bone fractures in the elderly (49). Loss of muscle strength has been correlated with a loss of Vitamin D receptors (VDR) in muscle cells (50). Supplemental Vitamin D of at least 800 IU per day may result in a clinically significant increase in VDR in muscle cells which may be in part be the mechanism whereby other studies have shown improvement in body-sway, muscle strength and falling risk were seen with Vitamin D supplementation at this level (51). While this muscular weakness associated with Vitamin D may not be surprising at classical Vitamin D deficiency levels (blood $25OH\text{-}VitD_3$ of <15 ng/mL), Bischoff-Ferrari et al continued to see improvement in lower extremity function up to and beyond 40 ng 25OH-VitD3/mL which are levels well above what previously might have been thought necessary for maximal benefit (52). This observation has been confirmed by other researchers that in fact minimal Vitamin D levels necessary to prevent rickets do not allow for maximal physical performance (53). A recent editorial in *American Journal of Clinical Nutrition* stated that all the literature available would indicate a $25OH\text{-}VitD_3$ level of at least 30 ng/mL is most optimal for health and disease (54).

While the exact mechanism is still unclear, it is clear that both the active metabolite, $1,25OH_2\text{-}VitD_3$ and its precursor, 25OH-VitD3, play a significant role in normal functioning of muscle. Muscle contains VDRs for $1,25OH_2\text{-}VitD_3$, found in both the nucleus and at the cell membrane (55-57) and these are also involved in non-specific binding 25OH-VitD3 as well (58). Studies by Haddad and Birge, published in the 1970s, show that feeding $D_3$ to vitamin D deficient rats 7 hours prior to measurement increased protein synthesis as measured by $^3$H-leucine incorporation into muscle cell proteins. However, when the muscles were removed from the Vitamin D deficient rats and studied, only 25-OH Vit $D_3$ acts directly in the muscles (58-60).

Early clinical evidence pointed to a reversible myopathy associated with Vitamin D deficiency (61). Vitamin D receptors were discovered in muscle tissue, thus providing direct evidence of Vitamin D's effect on muscle function (51, 62). Muscle biopsies in adults with Vitamin D deficiency exhibit mainly type II muscle fiber atrophy (63). Type II fibers are important because they are the first initiated to prevent a fall. A recent randomized controlled study found that daily supplementation of 1,000 IU of Vitamin $D_2$ in elderly stroke survivors resulted in an increase in mean type II fiber diameter and in percentage of type II fibers (64). There was also a correlation between serum 25OH-VitD3 level and type II fiber diameter.

Vitamin D conveys its action by binding to VDR. VDR is expressed in particular stages of differentiation from myoblast to myotubes (55, 65, 66). Two different VDRs have been described. One is located at the nucleus and acts as a nuclear receptor and the other is located at the cell membrane and acts as a cellular receptor. VDR knockout mice are characterized by a reduction in both body weight and size as well as impaired motor coordination (67). The nuclear VDR is a ligand-dependent nuclear transcription factor that belongs to the steroid-thyroid hormone receptor gene super-family (68). Bischoff et al (69) reported the first in situ detection of VDR in human muscle tissue with significant associated intranuclear staining for VDR. Once $1,25OH_2\text{-}VitD_3$ binds to its nuclear receptor, it causes changes in mRNA transcription and subsequent protein synthesis (70).

The genomic pathway has been known to influence muscle calcium uptake, phosphate transport across the cell membrane, phospholipid metabolism, and muscle cell proliferation and differentiation. 1,25OH-VitD$_3$ regulates muscle calcium uptake by modulating the activity of calcium pumps in sacroplasmic reticulum and sacrolemma (61). Modifications of calcium levels impact muscle function (71). In vitro experiments support these findings by demonstrating an increased uptake of $^{45}$Ca in cells exposed to physiological levels of 1,25OH$_2$-VitD$_3$ (72). The calcium binding protein calbindin D-9K is synthesized as a result of activation of nuclear VDR (62). 1,25OH$_2$-VitD$_3$ plays a role in regulating phosphate metabolism in myoblasts by accelerating phosphate uptake and accumulation in cells. 1,25OH$_2$-VitD$_3$ acts rapidly, presumably through cell membrane VDRs (56, 57). While binding to these receptors, there is an activation of second-messenger pathways (G-proteins, cAMP, inositol triphosphate, arachidonic acid) (73-75) or the phosphorylation of intracellular proteins. These would in turn activate protein kinase C (PKC), leading to release of calcium into muscle cells, and ultimately resulting in active transport of Ca into the sacroplasmic reticulum by Ca-ATPase. This process is important for muscle contraction. Additionally, PKC affects enhancements of protein synthesis in muscle cells (76). Recent data (77) indicate that 1,25OH-VitD3 has a fast activation of mitogen-activated protein kinase (MAPK) signaling pathways, which in turn forward signals to their intracellular targets that effect the initiation of myogenesis, cell proliferation, differentiation, or apoptosis.

Vitamin D may also regulate formation and regeneration of tight junctions and neuromuscular junctions. In vitro studies that found that Vitamin D regulates expression of VDR and the neural growth factor (NGF) in Schwann cells (78). Recent studies have shown that Vitamin D enhances glial cell line-derived neurotrophic factor (GDNF) in rats and that this may have beneficial effects in neurodegenerative disease (79). Therefore, Vitamin D could act through several mechanisms of cellular function and neural interaction to improve overall muscle strength and function.

A need exists for a composition and methods to increase muscle mass and improve function and strength. The present invention comprises a composition and methods of using a combination of Vitamin D and HMB that results in such an increase in muscle mass and improvement in strength and function.

SUMMARY OF THE INVENTION

One object of the present invention is to provide a composition for increasing muscle mass, strength, or functionality.

Another object of the present invention is to provide methods of administering a composition for increasing muscle mass, strength or functionality.

These and other objects of the present invention will become apparent to those skilled in the art upon reference to the following specification, drawings, and claims.

The present invention intends to overcome the difficulties encountered heretofore. To that end, a composition comprising HMB and Vitamin D is provided. The composition is administered to a subject in need thereof to increase muscle mass, strength and functionality. All methods comprise administering to the animal HMB and Vitamin D.

BRIEF DESCRIPTION OF THE DRAWINGS

FIG. 1a is a graph showing the changes in muscle mass in subjects depending on Vitamin D status.

FIG. 1b is a graph showing overall knee strength based on Vitamin D status with administration of HMB.

FIG. 2a is a graph showing serum Vitamin D levels in subjects.

FIG. 2b is a graph showing knee extension strength in subjects.

FIG. 2c is a graph showing an eight week performance index in subjects.

FIG. 3 shows the Protein:DNA ratio and protein degradation in C$_2$C$_{12}$ cells.

FIG. 4a is a graph showing serum Vitamin D levels in subjects.

FIG. 4b is a graph showing urine HMB excretion in subjects.

DETAILED DESCRIPTION OF THE INVENTION

The present invention comprises a combination of HMB and Vitamin D that has a synergistic effect and improves overall muscle strength and function. The combination of HMB and Vitamin D results in significant enhancements in overall muscle mass, function and strength. This combination can be used on all age groups seeking enhancement in overall muscle mass, function and strength. The following methods describe and show increased overall muscle mass, function and strength even in non-exercising animals.

One specific use HMB and Vitamin D is in the older or elderly population. Current estimates place a large portion of the older population at risk for falls with potential significant associated morbidities. The combination of HMB and Vitamin D specifically targets muscle mass, strength and function and consequently may produce significant improvement in health, quality of life, and in particular, decreased falls and injury in this group.

The younger population also benefits from the administration of HMB and Vitamin D, in part due to the widespread occurrence of Vitamin D deficiency. Women also benefit from the administration of HMB and Vitamin D as women are prone to Vitamin D deficiency.

Newborn babies and children twelve months and younger can benefit from the administration of HMB and Vitamin D. Baby formula is Vitamin D fortified, and the American Academy of Pediatrics (AAP) recommends that all infants, children and adolescents take in enough Vitamin D through supplements, formula or cow's milk to prevent complications from deficiency of this vitamin.

The present invention provides a composition comprising HMB and Vitamin D. The composition is administered to an animal in need of improvement in overall muscle mass, strength or function.

The composition of HMB and Vitamin D is administered to an animal in any suitable manner. Acceptable forms include, but are not limited to, solids, such as tablets or capsules, and liquids, such as enteral or intravenous solutions. Also, the composition can be administered utilizing any pharmaceutically acceptable carrier. Pharmaceutically acceptable carriers are well known in the art and examples of such carriers include various starches and saline solutions. In the preferred embodiment, the composition is administered in an edible form.

The composition of HMB and Vitamin D includes administration of the composition as baby formula and nutrition drinks for all ages.

β-hydroxy-β-methylbutyric acid, or β-hydroxy-isovaleric acid, can be represented in its free acid form as $(CH_3)_2(OH)CCH_2COOH$. The term "HMB" refers to the compound having the foregoing chemical formula, in both its free acid and salt forms, and derivatives thereof. While any form of HMB can be used within the context of the present invention, preferably HMB is selected from the group comprising a free acid, a salt, an ester, and a lactone. HMB esters include methyl and ethyl esters. HMB lactones include isovalaryl lactone. HMB salts include sodium salt, potassium salt, chromium salt, calcium salt, magnesium salt, alkali metal salts, and earth metal salts.

Methods for producing HMB and its derivatives are well-known in the art. For example, HMB can be synthesized by oxidation of diacetone alcohol. One suitable procedure is described by Coffman et al., *J. Am. Chem. Soc.* 80: 2882-2887 (1958). As described therein, HMB is synthesized by an alkaline sodium hypochlorite oxidation of diacetone alcohol. The product is recovered in free acid form, which can be converted to a salt. For example, HMB can be prepared as its calcium salt by a procedure similar to that of Coffman et al. in which the free acid of HMB is neutralized with calcium hydroxide and recovered by crystallization from an aqueous ethanol solution. The calcium salt of HMB is commercially available from Metabolic Technologies, Ames, Iowa.

CaHMB has historically been the preferred delivery form of HMB. Previously, numerous obstacles existed to both extensive testing and commercial utilization of the free acid form of HMB, and since it was thought there was no difference between the two forms from a pharmacokinetic perspective, the calcium salt was adopted as a commercial source of HMB. Until recently packaging and, in particular, distribution of dietary supplements has been better suited to handle nutrients in a powdered form and therefore the calcium salt of HMB was widely accepted. HMB-acid is a liquid and much more difficult to deliver or incorporate into products.

Currently, the manufacturing process for HMB has allowed for HMB free acid to be produced in a purity that allows for oral ingestion of the HMB free acid. Besides having a commercial source that is pure enough for oral ingestion, the HMB-acid needs to be buffered for oral ingestion, a process which only recently was determined due to the factors listed above which precluded previous use of HMB-acid.

It was assumed that ingestion of CaHMB would result in a rather quick dissociation of HMB from the calcium salt form. However, a recent study and corresponding patent application (U.S. App. Publication No. 20120053240) has shown that HMB in the free acid form has rather unique pharmacokinetic effects when compared to CaHMB ingestion. Use of HMB free acid (also called HMB-acid) improves HMB availability to tissues and thus provides a more rapid and efficient method to get HMB to the tissues than administration of CaHMB.

Vitamin D is present in the composition in any form. In the preferred embodiment, Vitamin $D_3$ (cholecalciferol) is administered, but the invention is not limited to that form of Vitamin D. While Vitamin $D_3$ is the synthesized and preferred form of Vitamin D for mammals, mammals can also use supplemental Vitamin $D_2$. Vitamin $D_2$ may be less potent than Vitamin $D_3$, hence additional $D_2$ may be required in order to raise blood levels of 25-OH Vit$D_2$.

When the composition is administered orally in an edible form, the composition is preferably in the form of a foodstuff or pharmaceutical medium, more preferably in the form of a foodstuff. Any suitable foodstuff comprising the composition can be utilized within the context of the present invention. In order to prepare the composition as a foodstuff, the composition will normally be blended with the appropriate foodstuff in such a way that the composition is substantially uniformly distributed in the foodstuff. Alternatively, the composition can be dissolved in a liquid, such as water. Although any suitable pharmaceutical medium comprising the composition can be utilized within the context of the present invention, preferably, the composition is blended with a suitable pharmaceutical carrier, such as dextrose or sucrose, and is subsequently tabulated or encapsulated as described above.

Furthermore, the composition can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include amino acids and/or lipids. The amounts of the composition to be administered intravenously can be similar to levels used in oral administration. Intravenous infusion may be more controlled and accurate than oral administration.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an eight week time period). The combination of HMB and Vitamin D can be administered over an extended period of time, such as months or years.

It will be understood by one of ordinary skill in the art that HMB and Vitamin D do not have to be administered in the same composition to perform the claimed methods. Stated another way, separate capsules, pills, mixtures, etc. of Vitamin D and of HMB may be administered to a subject to carry out the claimed methods.

Any suitable dose of HMB can be used within the context of the present invention. Methods of calculating proper doses are well known in the art. The dosage amount of HMB can be expressed in terms of corresponding mole amount of Ca-HMB. The dosage range within which HMB may be administered orally or intravenously is within the range from 0.01 to 0.2 grams HMB (Ca-HMB) per kilogram of body weight per 24 hours. For adults, assuming body weights of from about 100 to 200 lbs., the dosage amount orally or intravenously of HMB (Ca-HMB basis) can range from 0.5 to 30 grams per subject per 24 hours.

The amount of Vitamin D in the composition can be selecting an amount of Vitamin D within the range of greater than 500 IU, as the below examples indicate that 500 IU is the lower threshold for an effective amount in individuals with inadequate levels of Vitamin D in the bloodstream, yet not too much Vitamin D as to be toxic. While the examples indicate a threshold of 500 IU, lower amounts such as 400 IU, may be appropriate, in some individuals, to raise blood Vitamin D levels to an appropriate amount. In another embodiment, the amount of Vitamin D in the composition can be selecting an amount of Vitamin D within the range of greater than 400 IU, yet not too much Vitamin D as to be toxic. The toxic level of vitamin D is a person-specific amount and depends on a person's blood level of vitamin D. For example, administration of 100,000 IU of vitamin D may be toxic for healthy individuals, but not toxic for a person suffering from rickets. One of skill in the art will recognize toxicity levels for an individual. Further, the composition may include Vitamin D in amounts sufficient to raise blood levels of Vitamin D to at least around 25 ng/ml.

In the preferred embodiment, the composition comprises HMB in the form of its calcium salt, and Vitamin D in the form of 25-0H Vit $D_3$. Preferably, a composition in accordance with the present invention comprises HMB in an amount from about 0.5 g to about 30 g and Vitamin D in an amount greater than 500 IU, but not in an amount high enough to be toxic. One range of Vitamin D in accordance with this invention is around 1000 IU to around 4000 IU. For examples, 1001 IU, 1002 IU, 1003 IU . . . 1995 IU, 1996 IU, 1997 IU, 1998 IU, 1999 IU, 2000 IU, 2001 IU, 2002 IU, 2003 IU, 2004 IU, 2005 IU . . . 0.3997 IU, 3998 IU, 3999 IU, and all numbers between around 1000 IU and 4000 IU and not otherwise stated.

In another example, a range of Vitamin D in accordance with this invention is around 400 IU to around 100,000 IU. The specific amount of vitamin D that is appropriate to administer to a particular individual routinely varies. A healthy individual likely requires supplementation with vitamin D in an amount lower than an individual with certain disease conditions. For example, it would be appropriate in some circumstances to administer vitamin D to an individual with rickets in an amount of 100,000 IU daily. One of skill in the art is able to readily determine the amount of vitamin D that should be given to a particular individual without causing toxicity.

The amount of vitamin D used in the present invention depends on the individual's vitamin D status. In some individuals, around 400-500 IU of vitamin D is all that would be required to achieve a serum blood level of around 25 ng/ml. In others, 2,000, 4,000 or even 100,000 IU of vitamin D may be required. For example, 400 IU, 40 IU, 405 IU, 450 IU, 500 IU, 550 IU, 1000 IU, 1001 IU, 2000 IU, 5000 IU, 10,000 IU, 20,000 IU, 50,000 IU, 75,000 IU and 100,000 IU and all numbers around and between 400 IU and 100,000 IU that have not been otherwise stated are included in this invention.

The Food and Nutrition Board at the Institute of Medicine of The National Academies has developed intake reference values for Vitamin D and other nutrients. These values include the Recommended Dietary Allowance ("RDA"), which is defined as the average daily level of intake sufficient to meet the nutrient requirements of nearly all (97%-98%) healthy people; and Adequate Intake ("AI"), which is established when evidence is insufficient to develop an RDA and is set at a level assumed to ensure nutritional adequacy. The RDA for Vitamin D is currently set at 600 IU, or 15 mcg, for males and females ages 1-70. For people over the age of 70, the RDA is set at 800 IU of vitamin D (20 mcg). For babies from 0-12 months, an AI has been established of 400 IU (10 mcg).

Daily Values (DVs) are established by the Food and Drug Administration (FDA) and are used on food and dietary supplement labels. DVs suggest how much of a nutrient serving of the food or supplement provides in the context of a total daily diet. DVs are presented on food and supplement labels as a percentage. The Daily Value for Vitamin D, based on a caloric intake of 2,000 calories, for adults and children age 4 years or more, is 400 IU. The Daily Value for Vitamin D is also 400 IU for infants, children less than 4 years old, and pregnant and lactating women.

These amounts are determined such that a large percentage of the population taking these amounts will have sufficient Vitamin D levels. Heaney et al. have determined that a dose of 400 IU per day will elevate serum $25(OH)D_3$ levels by 7.0 nmol/L (or 2.8 ng/mL) (99).

In one example of the present invention, the amount of vitamin D used can be expressed in terms of the Recommended Dietary Allowance (RDA), Adequate Intake (AI), and/or Daily Value (DV). For example, the present invention includes compositions of HMB and Vitamin D in an amount around at least as much as the Recommended Daily Allowance of RDA; compositions of HMB and Vitamin D in an amount around at least as much as the Daily Value; and compositions of HMB and Vitamin D in an amount around at least as much as the Adequate Intake.

The amount of vitamin D needed to reach appropriate blood serum levels of vitamin D in accordance with the present invention may routinely vary from person to person, and determination of the optimum amount in each instance can be readily obtained by routine procedures.

In an additional embodiment, the composition in accordance with the present invention comprises HMB in an amount from about 0.5 g to about 30 g and Vitamin D in an amount sufficient to increase circulating blood levels of 25OH-VitD3 or 25-OH $VitD_2$, depending on the form supplemented, to at least about 25 ng/ml.

In general, an amount of HMB and vitamin D in the levels sufficient to improve overall muscle strength, function, and overall mass is administered for an effective period of time.

The invention provides a method of administering a composition of HMB and Vitamin D to an animal such that the animal's muscle mass increases. The animal may or may not engage in exercise. Exercising in conjunction with the administration of HMB and Vitamin D results in an even greater improvement in strength and muscle function, but exercise is not necessary to improve strength and muscle function. The amount of HMB and Vitamin D in the composition administered that are effective for increasing the animal's muscle mass can be determined in accordance with methods well-known in the art. In one embodiment, the effective amount of HMB in the composition may be from about 0.5 g to about 30 g and the effective amount of Vitamin D in the composition may be from greater than about 500 IU per 24 hour period. In another embodiment, the effective amount of HMB is the same, and the effective amount of Vitamin D is that which is sufficient to increase blood levels of Vitamin D to at least about 25 ng/ml.

The invention provides a method of administering a composition of HMB and Vitamin D to an animal such that the animal's strength increases. The animal may or may not engage in exercise. The amount of HMB and Vitamin D in the composition administered that are effective for increasing the animal's muscle mass can be determined in accordance with methods well-known in the art. In one embodiment, the effective amount of HMB in the composition may be from about 0.5 g to about 30 g and the effective amount of Vitamin D in the composition may be from greater than about 500 IU per 24 hour period. In another embodiment, the effective amount of HMB is the same, and the effective amount of Vitamin D is that which is sufficient to increase blood levels of Vitamin D to at least about 25 ng/ml.

The invention further comprises a method of administering a composition of HMB and Vitamin D in an effective amount for improving muscle function. The amount of HMB and Vitamin D in the composition administered that are effective for increasing the animal's muscle mass can be determined in accordance with methods well-known in the art. In one embodiment, the effective amount of HMB in the composition may be from about 0.5 g to about 30 g and the effective amount of Vitamin D in the composition may be from greater than about 500 IU. In another embodiment, the effective amount of HMB is the same, and the effective amount of Vitamin D is that which is sufficient to increase blood levels of Vitamin D to at least about 25 ng/ml.

EXAMPLES

The following examples further illustrate the invention but should not be construed as in any way limiting its scope. For example, the amounts of HMB and Vitamin D administered and the duration of the supplementation are not limited to what is described in the examples.

These examples demonstrate the surprising result that the combination of vitamin D and HMB improves strength and muscle function. It was previously known that HMB supplementation increases muscle mass, but no corresponding improvement in strength and muscle function was seen with HMB alone. The examples demonstrate that when serum levels of Vitamin D reach appropriate levels, most typically through supplementation, muscle strength and function improve. The increases in strength, muscle mass, and improved muscle function described and observed in the examples below demonstrate that HMB and Vitamin D are synergistic; when vitamin D levels reach an adequate amount, administration of HMB works better, more effectively or more efficiently than HMB when administered without adequate vitamin D levels. A composition containing HMB and Vitamin D in sufficient amounts will be more efficient and more effective than a composition containing HMB that does not also include adequate amounts of Vitamin D. The studies below examine the effects of vitamin D levels on the efficacy of HMB as related to muscle function, strength and muscle mass, but the improved efficacy of HMB as described in this invention includes all known uses of HMB, including but not limited to the use of HMB for disease associated wasting, aging, cachexia, and nitrogen retention. Further, the efficacy of HMB as related to immune function and lowering cholesterol are also within the scope of this agreement.

Example 1

It is known that administration of HMB and amino acids, specifically arginine and lysine, administered to the non-exercising population results in significant increases in lean mass and improvement in protein turnover. Due to the increases in lean mass and improvement in protein turnover, it would be expected that administration of HMB and amino acids would also improve strength and function. Administration of HMB and amino acids alone, however, does not result in improvement in strength, function, or both. Instead, a gradual loss of handgrip and leg strength is observed. The following example demonstrates that the amount of Vitamin D in the bloodstream affects whether administration of HMB shows improvement in muscle strength and/or function. The data demonstrate that administration of HMB, arginine, and lysine (HMB/ARG/LYS) and Vitamin D is superior to administration of either HMB/ARG/LYS alone or Vitamin D alone. These results show a synergistic effect between HMB and Vitamin D for improving muscle strength and function.

Methods

The effects of HMB, arginine, and lysine (HMB/ARG/LYS) on strength and muscle function in the elderly was studied in both elderly men (n=38) and women (n=39) with an average age of 76.0±1.6 years (80). Subjects were randomly assigned to either treatment with HMB/ARG/LYS (n=40) or to an isonitrogenous control group (n=37) for a one year study. Supplements were taken once per day in the morning with breakfast and all supplements supplied 0.1 g ascorbic acid per day. The HMB/ARG/LYS contained 2 g CaHMB, 5 g arginine, and 1.5 g lysine. The control contained 5.6 g alanine, 0.9 g glutamic acid, 3.1 g glycine, and 2.2 g serine. The supplements were supplied as a ready to mix orange-flavored powder. Subjects weighing more than 68 kg were given supplements containing 1.5 times the dosage above to maintain close to 38 mg/kg body weight per day CaHMB intake as this has been shown to be an effective intake of HMB per day. Lean tissue mass was measured using two independent methods, bioelectrical-impedance analysis (BIA) and dual energy x-ray absorptiometry (DXA). Strength was measured in the upper and lower extremities.

The retrospective analysis of serum 25OH-VitD3 in the same cohort was performed and the data were stratified based upon the Vitamin D status of the subjects within each original treatment group. An "adequate Vitamin D status" was defined as serum 25OH-VitD3 level of ≥30 ng/mL (82-84). Consequently four cohorts were identified: (1) control-subjects with a 25OH-VitD3 level <30 ng/mL (n=25); (2) HMB/ARG/LYS subjects with a 25OH-VitD3 level <30 ng/mL (n=29); (3) control subjects with a 25OH-VitD3 level >30 ng/mL (n=12); and (4) HMB/ARG/LYS subjects with a 25OH-VitD3 level >30 ng/mL (n=11).

Statistics

The data, means and changes in means over the 12-month period, were analyzed using a mixed models procedure of the Statistical Analysis System for Windows (Release 8.02, SAS Institute, Cary, N.C.). A repeated measures analysis of variance (ANOVA) that included the initial time 0 values for the variable measured as a covariate and main effects of site, gender, and treatment. Lean body mass was analyzed using linear and quadratic time by treatment contrasts.

Results and Analysis

Supplementation with HMB/ARG/LYS resulted in statistically significant increases in muscle mass irrespective of the Vitamin D status (FIG. 1a). The 12-month increase in lean mass within the cohorts with 25OH-VitD3>30 ng/mL was 0.9 kg, and 0.7 kg in the cohorts with <30 ng/mL (FIG. 1a), which were not significantly different. However, regardless of Vitamin D status, there was a significant increase in lean mass over the year long supplementation (FIG. 1a inset, p=0.02). On the other hand there was significant divergence in muscle strength based upon Vitamin D status (FIG. 1b). Measurements of "Overall Knee Strength" showed that the HMB/ARG/LYS-supplemented group with 25OH-VitD3 level >30 ng/mL had significant improvements in muscle strength. When this group was compared with the other three cohorts, there was a 21% linear increase in strength (p<0.003).

Taken together, these results suggest a synergistic effect between the HMB-supplemented cocktail and Vitamin D. Although HMB/ARG/LYS supplementation increased muscle mass (fat-free-mass) regardless of Vitamin D status, strength was only increased with HMB/ARG/LYS supplementation when subjects had adequate Vitamin D status.

The combination of HMB/ARG/LYS and adequate Vitamin D status is necessary for and superior to either HMB/ARG/LYS alone or adequate Vitamin D alone based upon the controls with adequate Vitamin D in improving the strength and functionality of muscle. These results show a synergistic effect between HMB and Vitamin D for improving muscle strength and function.

Prior studies examining the effect of HMB on increasing muscle mass were not significantly improved in all study designs (published and unpublished). It is believed that Vitamin D status may not have been adequate to maximize muscle mass gains in these earlier studies in the HMB-supplemented subjects. This may be especially true in populations where low vitamin D status due to age, geographical location, dietary intake, or disease was in question. Consequently, supplementation with a combination of HMB and Vitamin D may not only increase muscle strength and functionality but also restore or increase muscle mass compared to supplementation of HMB alone.

Example 2

In this example, subjects were administered a combination of HMB and vitamin supplements.

Materials and Methods:

Elderly women (n=30) and men (n=16) were recruited into a double-blinded controlled study. The older adults were recruited from two locations in South Dakota: Brookings and Sioux Falls. The subjects underwent an initial screening and were randomized to treatments. Testing consisted of an initial (0 weeks) and follow-up testing at 4, 8 and 12 weeks over the course of the 12-week study.

Prior to the start of the experimental period, we randomly assigned nutritional supplements to each subject using computer-generated random numbers in a double-blind fashion. Treatments were arranged in a 2×2 factorial design with two levels of HMB (0 & 3.0 g/d) and two levels of Vitamin D (0 & 2,000 IU/d). We assigned subjects to one of the following four treatments:

(1) Control
(2) HMB (calcium salt), 3.0 g/day
(3) 2,000 IU Vitamin D/day
(4) HMB, 3.0 g/day+2,000 IU Vitamin D.

The treatments were supplied in capsules of equal size and color and contained equal amounts of calcium and phosphorus. The subjects were instructed to take three capsules two times a day. Each subject was supplied with a one-week supply of the supplement, allocated by subject number and returned each week for an additional 1-week supply.

The exercise testing and training session was supervised by trained research associates. Resting heart rate and blood pressure measurements were obtained prior to strength measurements. Enrolled individuals participated in an exercise training program consisting of strength training exercises with Theraband® stretch cords (resistance training) and jumping. The equipment consisted of items that can easily be used at home. Exercise sessions were 3 times a week for 12 weeks. Each exercise session was about 45-60 minutes. Testing sessions were performed at 0, 4, 8, and 12 weeks. Each testing session lasted ~60 minutes.

The strength program incorporated the following exercises: bicep curls, triceps extensions, chair squats, calf raises, ankle dorsiflexion, shoulder front raises and lateral raises, latissimus dorsi pull-down, chest press, seated row, knee flexion and extension, and hip flexion. For each of the 12 exercises, the participants completed 3 sets of isotonic movement, 2 sets of 20 repetitions, and a final set to failure. When the $3^{rd}$ set could be performed for 20 repetitions in good form, the resistance was increased by moving to the next color of the resistance band. Between each set, participants performed a set of hops or small jumps. Initially, 5 hops/jumps were performed following each set. The number of hops/jumps was increased by 5 every 3 weeks until 25 hops/jumps were achieved. Subjects remained at 25 hops/jumps between sets for the remainder of the study. The number of hops/jumps was reduced or omitted if there are any complaints regarding joint pain. The resistance bands had been shown to safely increase strength and functionality when used in an older adult population (87-90).

Body composition measurements were obtained at 0, 4, 8, and 12 weeks. Measurements of strengths of quadriceps (extension/flexion) and elbows (extension/flexion) were obtained using the BIODEX Isokinetic Dynamometer. Handgrip strength was measured using a handgrip dynamometer. Peak torque for knee extension and flexion was measured at 60, 90 and 120°/sec. Peak torque for elbow extension and flexion was measured at 60 and 120°/sec.

Functionality tests included: "Get-up-and-Go" performance (speed and gate), and "Get-up" performance. The "Get-up-and-Go" test consisted of timed measurements of the subject's starting from a seated position, standing, walking forward 3 meters, turning around, walking back to the chair, and sitting down. The "Get-up" test consisted of the subject standing upright from a seated position as many times as possible within 30 seconds. The complete descriptions and standardization of the tests are outlined in the *Physical Dimensions of Aging* by Waneen W. Spirduso (Human Kinetics, 1995).

A muscular performance index was calculated by summing the percentage change from baseline for Get-up-and-Go, Get-up, handgrip, peak torque for knee extension and flexion (60, 90 and 120°/sec) and peak torque for elbow extension and flexion (60°/sec).

At 0, 4, 8, and 12 weeks blood samples were taken from a superficial arm vein into Vacutainers™ (Becton Dickinson, Vacutainer Systems, Rutherford, N.J.) after an overnight fast. Serum was collected and used to measure 25OH-VitD3 using a fully automated antibody-based chemiluminescence assay (DiaSorin Inc., Stillwater, Minn.).

Least Squares Mean±SEM were calculated strength and functionality changes in each variable over the 12-week period. The mixed models procedure of the Statistical Analysis System for Windows (Release 9.1, SAS Institute, Cary, N.C.) was used to analyze the data. Analysis of Covariance was used with main effects of HMB, Vitamin D and the HMB*Vitamin D interaction. Data were adjusted using the initial serum 25OH-VitD3 concentration as the covariate. The hypothesize was that the combination of HMB and Vitamin D supplementation will result in a greater improvements in strength and functionality as compared to control, HMB, or Vitamin D-treated subjects. This synergistic effect was tested with pre-planned one-tail t-test in a post-hoc analysis. Statistical significance was determined for $p<0.05$ and a trend was determined for $0.05<p<0.10$.

Results and Discussion:

A total of 43 subjects completed the 12-week and one subject completed the 8-weeks of the study and was included in the analysis. Two subjects dropped from the study prior to the 4-week follow-up visit and were not used in the analysis. The subjects that dropped from the study did so because of the demanding commitment of a 12-week training study and not due to any adverse events. The subject characteristics of the 44 subjects used in the analysis are presented in Table 1.

TABLE 1

Subject Characteristics

| Item | Control | HMB | VitD$_{2000}$ | HMB + VitD$_{2000}$ |
|---|---|---|---|---|
| n | 11 | 11 | 11 | 11 |
| Age | 73.4 ± 2.6 (62-87) | 73.5 ± 3.0 (60-89) | 72.1 ± 2.8 (61-96) | 68.5 ± 2.5 (60-84) |
| M/F | 3/8 | 4/7 | 4/7 | 4/7 |
| *25OH-VitD$_3$ | 29.2 ± 3.0 (12.4-46.5) | 25.4 ± 3.0 (12.2-39.7) | 24.0 ± 2.0 (11.7-34.3) | 27.4 ± 3.0 (15.1-42.9) |
| #Leg Strength, Extension | 73.9 ± 9.6 (33-148) | 64.1 ± 7.4 (23-98.3) | 74.8 ± 10.0 (24.7-133) | 83.1 ± 10.6 (40.5-146.1) |
| Flexion | 51.4 ± 6.2 (23-95) | 43.6 ± 5.3 (14-61) | 55.9 ± 6.1 (13.8-83) | 51.8 ± 7.7 (18-99) |

Data are expressed as Mean ± SE (min-max)
*Baseline value
Baseline Peak Torque @ 60°/sec The average 25OH-VitD3 concentration at wk 0 was 26.5 ng/ml. Subjects treated with 2000 IU of Vitamin D per day increased their serum 25OH-VitD3 level by 10.7 ng/mL (FIG. 2a). However, subjects either supplemented with a control or HMB alone decreased their serum 25OH-VitD3 level by 2.0 ng/mL. A clean catch urine sample was used to test for supplement compliance. Subjects supplemented with HMB had a 50 fold increase in urinary HMB concentration whereas the subjects not consuming a HMB supplement had no increase urinary HMB concentration.

The effects of the combination of HMB and Vitamin D on knee extension strength (peak torque, 60°/sec is presented in FIG. 2b. Supplementation with HMB+Vitamin D (7.28±5.03 nm) in older adults results in a statistically greater eight week increase in knee extension strength as compared to control-treated subjects, P<0.05 (~6.28±5.02 nm). Neither the HMB alone nor the Vitamin D-treated subjects increased knee extension strength when compared to the control-treated subjects. These data support our hypothesis that the combination of HMB+Vitamin D would be synergistic on muscular strength.

Although not significant the performance index tends supports these observations (see FIG. 2c). The performance index not only includes leg strength measurements but also functionality, hand grip strength, and elbow strength. These strength and function measurements are summed into one overall performance index. The combination of HMB+Vitamin D resulted in a 146% increase in the performance index over the control. Whereas HMB and Vitamin D supplementation resulted in only a 35 and 58% increase, respectively, when compared to older adults supplemented with the control treatment.

Implications:

These data from a prospective study in older adults support the hypothesis that the combination of HMB and Vitamin D supplementation is synergistic, and resulted in significant improvements in knee muscle strength and overall performance index. These data support the observation from our retrospective study in an elderly population supplemented with HMB, Arginine, and Lysine. Muscular strength increases only occur with HMB, Arginine, and Lysine in older adults with adequate Vitamin D. In conclusion, the combination HMB and Vitamin D is superior to either HMB or Vitamin D alone and is therefore synergistic. These findings are important as the Vitamin D status in approximately 66% of the elderly population is low and leads to a decrease in muscular strength and function. The loss of strength and function leads to an increase in falls and fractures, poor quality of life and will ultimately impact health care costs.

Example 3

In this example, cell culture studies were performed to analyze the effects of HMB and vitamin D on protein, DNA and protein turnover in muscle cell cultures.

Recent in vitro studies have shown that HMB decreases protein breakdown. In one study HMB attenuated proteolysis-inducing factor (PIF) activation and increased gene expression of the ubiquitin-proteasome pathway in murine myotubes, thereby reducing protein degradation (91). Other studies also suggest HMB may influence protein synthesis through the mTOR pathway (92). Early studies have also suggested that vitamin D affects protein metabolism (93). Vitamin D also binds a VDR found in the nucleus of muscle cells and regulates gene expression (94). We hypothesize that HMB and vitamin D both have effects on muscle cells and that if they act through independent mechanisms there could be a synergistic effect on either protein, DNA or protein turnover in the cells.

Methods

Mouse C2C12 skeletal muscle cell myoblasts were grown in culture under standard conditions and fused into myotubes following the methods of Menconi et al. (95). Four separate studies were conducted during different weeks. The first 3 studies consisted of 4 replicate dishes per treatment and the fourth study consisted of 6 replicate dishes per treatment. The treatments were applied to the cells during the 24 h measurement period. Treatments applied were control, 25OH-VitD3 (200 ng/mL), HMB (200 µM HMB as Ca(HMB)$_2$, and the combination of HMB and 25OH-VitD3. Dexamethasone (100 nM) was added to the culture medium during the treatment/measurement period to stimulate protein degradation. Calcium in the form of calcium chloride was added to the control and 25OH-VitD3 treatments so that all the treatments were balanced for calcium. For measurement of protein degradation during the treatment period, leucine free medium was obtained to which [5,5,5]$^2$H$_3$-leucine was added so that the isotopes of leucine (natural leucine and [1-$^{13}$C]-leucine) could be measured as they were released into the medium through the protein degradation process. The measurement medium was sampled at 2 and 24 h and samples stored at −80° C. until analyzed. The samples were analyzed for leucine using a gas chromatography (model 6890, Hewlett Packard, Palo, Calif.) mass spectrometry (model 5973, Hewlett Packard, Palo, Calif.) and the gas chromatography column used for the analysis was a Zebron ZB-5. (Phenomenex, Torrence, Calif.). Natural leucine, [1-$^{13}$C]-leucine, and [5,5,5$^2$H$_3$]-leucine were monitored at 302, 303, and 305 AMU, respectively. Corrections for sampling at 2 h and for leucine utilization from the measurement media were made. The amount of the leucine isotopes released was also corrected for utilization (transamination and/or protein synthesis) (96). Concentrations of proteins were analyzed following the microplate assay instructions using a Pierce BCA protein assay kit (Thermo Scientific, Rockford, Ill.). DNA was measured flourometrically using the Quant-iT™ dsDNA assay kit from Invitrogen (Carlsbad, Calif.).

Statistics

Each cell culture dish was considered an experimental unit for analysis. Data presented are least square means and data were analyzed using General Linear Models in the Statistical Analysis System for Windows (Release 8.02, SAS Institute, Cary, N.C.). Main effects of experiment, HMB, vitamin D, and the interaction of HMB and vitamin D were included in the model. Post-hoc least square means analysis was performed for individual treatment means.

Results and Analysis

After the 24 h treatment period there were no treatment main effects on total protein content in the culture dishes. There were no significant treatment main effects for DNA content. Protein:DNA ratio with the combination of HMB and 25OH-VitD3 (FIG. 3) was significantly greater than either the control group or either treatment group alone and the interaction was significant (p<0.003). This significant interaction response for the main effects would indicate a synergistic response of HMB and 25OH-VitD3 on protein: DNA ratio. Measures of protein degradation and protein synthesis showed no significant main effects of treatment on protein degradation measured either by natural or $[1-^{13}C]$-leucine release into the medium from the cells. There was, however, a strong trend for the interaction between HMB and 2=5OH VitD$_3$ on protein degradation measured by $[1-^{13}C]$-leucine (p<0.08, FIG. 3). Post-hoc least square means analysis of the effects of HMB alone showed a significant decrease in protein degradation of 7.6 and 6.3% as measured by natural leucine and $[1-^{13}C]$-leucine, respectively (p<0.06). HMB and 25OH-VitD3 combination treatment also decreased protein degradation, but the lack of neither a significant interaction nor a 25OH-VitD3 main treatment effect would indicate the effect was due primarily to HMB. Protein synthesis and leucine utilization as measured by disappearance of $[5,5,5-^2H_3]$-leucine from the media showed no differences among treatments. The current series of studies show that HMB and 25OH-VitD3 combination increases protein:DNA ratio and that HMB decreases protein degradation. These both are indications that the cell is producing more proteins, possibly of a functional nature. The data also show that the HMB decreases dexamethasone stimulated protein degradation in both slower and faster turnover protein pools natural and $[1-^{13}C]$-leucine labels, respectively. Vitamin D tended to decrease dexamethasone stimulated protein degradation in only the faster turnover protein pool. These could indicate that vitamin D affects synthesis of functional proteins as vitamin D has been shown in other cell types to increase cell adhesion proteins (97, 98). In conclusion, the HMB+vitamin D combination was synergistic in increasing protein:DNA ratio in the cells and supports our hypothesis.

Example 4

The amount of Vitamin D administered with HMB must be in an effective amount to raise the blood level of Vitamin D. In this example, it is demonstrated that 500 IU of Vitamin D does not sufficiently raise the blood level of Vitamin D; this finding however, is based on the subjects in this study. As stated hereinabove, the amount of Vitamin D necessary to raise blood serum levels of Vitamin D to an adequate amount depends on the individual's Vitamin D status; in some instances, as little as 400 IU of Vitamin D is an appropriate amount to raise blood levels to around at least 25 ng/ml.

Subjects with adequate Vitamin D (plasma 25OH-VitD3 levels >30 ng/ml) manifested significant improvements in muscle function, while those with biochemical evidence of Vitamin D deficiency (25OH-VitD$_3$ levels <30 ng/ml) failed to show improvements in muscle strength and functionality. While muscular weakness associated with Vitamin D may not be surprising at classical Vitamin D deficiency levels (blood 25OH-VitD3 of <15 ng/mL), Bischoff-Ferrari et al continued to see improvement in lower extremity function up to and beyond 40 ng 25OH-VitD3/mL which are levels well above what previously might have been thought necessary for maximal benefit (11). Therefore, supplementation Vitamin D should be adequate to raise 25OH-VitD3. FIG. 4a demonstrates the blood 25OH-VitD3 response when a control, or supplement containing either 500 or 2000 IU of Vitamin D were given daily for 12 weeks in older adult over 65 years of age. Subjects supplemented with either the control or 500 IU of Vitamin D for 12 weeks did not increase blood 25OH-VitD3. Whereas subjects supplemented with 2000 IU of Vitamin D increased blood levels by over 10 ng/mL in 12 weeks. This supplementation established a blood level of 25OH-VitD3 level >30 ng/ml. FIG. 4b shows the urine levels of HMB in these subjects. In conclusion, 2000 IU of Vitamin D is sufficient to raise blood levels 25OH-VitD3, where 500 IU is inadequate. When Vitamin D levels are adequately raised, the use of HMB results in an increase in strength and muscle function.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

LITERATURE CITED

1. Krebs, H. A. & Lund, P. (1977) Aspects of the regulation of the metabolism of branched-chain amino acids. Advan. Enzyme Regul. 15: 375-394.
2. Harper, A. E., Benevenga, N. J. & Wohlhueter, R. M. (1970) Effects of ingestion of disproportionate amounts of amino acids. Physiol. Rev. 53: 428-558.
3. Nissen, S. L. & Abumrad, N. N. (1997) Nutritional role of the leucine metabolite β-hydroxy-β-methylbutyrate (HMB). J. Nutr. Biochem. 8: 300-311.
4. Nissen, S., Sharp, R., Ray, M., Rathmacher, J. A., Rice, J., Fuller, J. C., Jr., Connelly, A. S. & Abumrad, N. N. (1996) The effect of the leucine metabolite β-hydroxy β-methylbutyrate on muscle metabolism during resistance-exercise training. J. Appl. Physiol. 81(5): 2095-2104.
5. Nissen, S., Van Koevering, M. & Webb, D. (1990) Analysis of β-hydroxy-β-methyl butyrate in plasma by gas chromatography and mass spectrometry. Anal. Biochem. 188: 17-19.
6. Frexes-Steed, M., Warner, M. L., Bulus, N., Flakoll, P. & Abumrad, N. N. (1990) Role of insulin and branched-chain amino acids in regulating protein metabolism during fasting. Am. J. Physiol. (Endocrinol. Metab.) 258: E907-E917.
7. Robinson, W. G., Bachhawat, B. K. & Coon, M. J. (1954) Enzymatic carbon dioxide fixation by senecioyl coenzyme A. Fed. Proc. 13: 281.
8. Rudney, H. & Farkas, T. G. (1955) Biosynthesis of branched chain acids. Fed. Proc. September: 757-759.
9. Rabinowitz, J. L., Dituri, F., Cobey, F. & Gurin, S. (1955) Branched chain acids in the biosynthesis of squalene and cholesterol. Fed. Proc. 14: 760-761.

10. Coon, M. J. (1955) Enzymatic synthesis of branched chain acids from amino acids. Fed. Proc. 14: 762-764.
11. Gey, K. F., Pletsher, A., Isler, O., Ruegg, R. & Wursch, J. (1957) The influence of isoperenic C5 and C6 compounds upon the acetate incorporation into cholesterol. Helvetica Chim. Acta 40: 2369 (abs.).
12. Gey, K. F., Pletsher, A., Isler, O., Ruegg, R. & Wursch, J. (1957) Influence of iosoprenoid C5 and C6 compounds on the incorporation of acetate in cholesterol. Helvetica Chim. Acta 40: 2354-2368.
13. Isler, O., Ruegg, R., Wursch, J., Gey, K. F. & Pletsher, A. (1957) Biosynthesis of cholesterol from β,τ-dihydroxy-β-methylvaleric acid. Helvetica Chim. Acta 40: 2369 (abs.).
14. Zabin, I. & Bloch, K. (1951) The utilization of butyric acid for the synthesis of cholesterol and fatty acids. J. Biol. Chem. 192: 261-266.
15. Plaut, G. W. E. & Lardy, H. A. (1951) Enzymatic incorporation of C14-bicarbonate into acetoacetate in the presence of various substrates. J. Biol. Chem. 192: 435-445.
16. Bloch, K., Clark, L. C. & Haray, I. (1954) Utilization of branched chain acids in cholesterol synthesis. J. Biol. Chem. 211: 687-699.
17. Rudney, H. (1954) The synthesis of β-hydroxy-β-methylglutaric acid in rat liver homogenates. J. Am. Chem. Soc. 76: 2595.
18. Bachhawat, B. K., Robinson, W. G. & Coon, M. J. (1955) The enzymatic cleavage of beta-hydroxy-beta-methylglutaryl coenzyme a to aceto-acetate and acetyl coenzyme A. J. Biol. Chem. 216: 727-736.
19. McAllan, A. B. & Smith, R. H. (1984) The efficiency of microbial protein synthesis in the rumen and the degradability of feed nitrogen between the mouth and abomasum in steers given different diets. Br. J. Nutr. 51: 77-83.
20. Adamson, L. F. & Greenberg, D. M. (1957) The significance of certain carboxylic acids as intermediates in the biosynthesis of cholesterol. Biochim. Biophys. Acta 23: 472-479.
21. Jówko, E., Ostaszewski, P., Jank, M., Sacharuk, J., Zieniewicz, A., Wilczak, J. & Nissen, S. (2001) Creatine and β-hydroxy-β-methylbutyrate (HMB) additively increases lean body mass and muscle strength during a weight training program. Nutr. 17: 558-566.
22. Knitter, A. E., Panton, L., Rathmacher, J. A., Petersen, A. & Sharp, R. (2000) Effects of (3-hydroxy-β-methylbutyrate on muscle damage following a prolonged run. J. Appl. Physiol. 89(4): 1340-1344.
23. Gallagher, P. M., Carrithers, J. A., Godard, M. P., Schulze, K. E. & Trappe, S. W. (2000) β-Hydroxy-β-methylbutyrate ingestion, Part I: Effects on strength and fat free mass. Med Sci Sports Exerc 32(12): 2109-2115.
24. Ostaszewski, P., Kostiuk, S., Balasinska, B., Jank, M., Papet, I. & Glomot, F. (2000) The leucine metabolite 3-hydroxy-3-methylbutyrate (HMB) modifies protein turnover in muscles of the laboratory rats and domestic chicken in vitro. J. Anim. Physiol. Anim. Nutr. (Swiss) 84: 1-8.
25. Rathmacher, J. A., Zachwieja, J. J., Smith, S. R., Lovejoy, J. L. & Bray, G. A. (2001) The effect of the leucine metabolite $-hydroxy-$-methylbutyrate on lean body mass and muscle strength during prolonged bedrest. FASEB J 13: A909.
26. Panton, L. B., Rathmacher, J. A., Baler, S. & Nissen, S. (2000) Nutritional supplementation of the leucine metabolite β-hydroxy β-methylbutyrate (HMB) during resistance training. Nutr. 16(9): 734-739.
27. Slater, G., Jenkins, D., Logan, P., Lee, H., Vukovich, M. D., Rathmacher, J. A. & Hahn, A. G. (2001) b-hydroxy b-methylbutyrate (HMB) supplementation does not affect changes in strength or body composition during resistance training in trained men. Int. J. Sport Nutr. Exerc. Metab 11: 384-396.
28. Vukovich, M. D., Stubbs, N. B. & Bohlken, R. M. (2001) Body composition in 70-year old adults responds to dietary β-hydroxy-β-methylbutyrate (HMB) similar to that of young adults. J. Nutr. 131(7): 2049-2052.
29. Eley, H. L., Russell, S. T., Baxter, J. H., Mukherji, P. & Tisdale, M. J. (2007) Signaling pathways initiated by β-hydroxy-β-methylbutyrate to attenuate the depression of protein synthesis in skeletal muscle in response to cachectic stimuli. Am. J. Physiol Endocrinol. Metab 293: E923-E931.
30. Smith, H. J., Mukerji, P. & Tisdale, M. J. (2005) Attenuation of proteasome-induced proteolysis in skeletal muscle by β-hydroxy-β-methylbutyrate in cancer-induced muscle loss. Cancer Res. 65: 277-283.
31. Smith, H. J., Wyke, S. M. & Tisdale, M. J. (2004) Mechanism of the attenuation of proteolysis-inducing factor stimulated protein degradation in muscle by beta-hydroxy-beta-methylbutyrate. Cancer Res. 64: 8731-8735.
32. Eley, H. L., Russell, S. T. & Tisdale, M. J. (2008) Mechanism of Attenuation of Muscle Protein Degradation Induced by Tumor Necrosis Factor Alpha and Angiotensin II by beta-Hydroxy-beta-methylbutyrate. Am. J. Physiol Endocrinol. Metab 295: E1417-E1426.
33. Eley, H. L., Russell, S. T. & Tisdale, M. J. (2008) Attenuation of depression of muscle protein synthesis induced by lipopolysaccharide, tumor necrosis factor and angiotensin II by β-hydroxy-β-methylbutyrate. Am. J. Physiol Endocrinol. Metab 295: E1409-E1416.
34. Nissen, S. L. & Sharp, R. L. (2003) Effect of dietary supplements on lean mass and strength gains with resistance exercise: a meta-analysis. J Appl. Physiol 94: 651-659.
35. Kreider, R., Ferreira, M., Wilson, M. & Almada, A. (1999) Effects of calcium beta-hydroxy-beta-methylbutyrate (HMB) supplementation during resistance-training on markers of catabolism, body composition and strength. Int J Sports Med 20: 503-509.
36. Gallagher, P. M., Carrithers, J. A., Godard, M. P., Schutze, K. E. & Trappe, S. W. (2000) 3-Hydroxy-β-methylbutyrate ingestion, Part II: Effects on hematology, hepatic, and renal function. Med Sci Sports Exerc 32(12): 2116-2119.
37. Nissen, S., Panton, L., Sharp, R. L., Vukovich, M., Trappe, S. W. & Fuller, J. C., Jr. (2000) β-Hydroxy-β-methylbutyrate (HMB) supplementation in humans is safe and may decrease cardiovascular risk factors. J Nutr 130: 1937-1945.
38. Rathmacher, J. A., Nissen, S., Panton, L., Clark, R. H., Eubanks, M. P., Barber, A. E., D'Olimpio, J. & Abumrad, N. N. (2004) Supplementation with a combination of beta-hydroxy-beta-methylbutyrate (HMB), arginine, and glutamine is safe and could improve hematological parameters. JPEN J Parenter Enteral Nutr 28: 65-75.
39. Eubanks May, P., Barber, A., Hourihane, A., D'Olimpio, J. T. & Abumrad, N. N. (2002) Reversal of cancer-related wasting using oral supplementation with a combination of β-hydroxy-β-methylbutyrate, arginine, and glutamine. Am. J. Surg. 183: 471-479.
40. Clark, R. H., Feleke, G., Din, M., Yasmin, T., Singh, G., Khan, F. & Rathmacher, J. A. (2000) Nutritional treatment for acquired immunodeficiency virus-associated wasting using β-hydroxy-β-methylbutyrate, glutamine and arginine: A randomized, double-blind, placebo-controlled study. JPEN J Parenter Enteral Nutr 24(3): 133-139.
41. Baier, S., Johannsen, D., Abumrad, N. N., Rathmacher, J. A., Nissen, S. L. & Flakoll, P. J. (2009) Year-long changes in lean body mass in elderly men and women supplemented with a nutritional cocktail of β-hydroxy-β-methylbutyrate (HMB), arginine, and lysine. JPEN 33: 71-82.
42. Webb, A. R., Kline, L. & Holick, M. F. (1988) Influence of season and latitude on the cutaneous synthesis of vitamin D3: exposure to winter sunlight in Boston and Edmonton will not promote vitamin D3 synthesis in human skin. J Clin. Endocrinol. Metab 67: 373-378.
43. Holick, M. F. (2007) Vitamin D deficiency. N. Engl. J. Med. 357: 266-281.
44. Heaney, R. P., Dowell, M. S., Hale, C. A. & Bendich, A. (2003) Calcium absorption varies within the reference range for serum 25-hydroxyvitamin D. J. Am. Coll. Nutr. 22: 142-146.
45. Heaney, R. P. (2008) Vitamin D in Health and Disease. Clin. J. Am. Soc. Nephrol. 3: 1535-1541.
46. Jones, G. (2007) Expanding role for vitamin D in chronic kidney disease: importance of blood 25-OH-D levels and extra-renal 1alpha-hydroxylase in the classical and nonclassical actions of 1alpha,25-dihydroxyvitamin D(3). Semin. Dial. 20: 316-324.
47. Zehnder, D., Bland, R., Williams, M. C., McNinch, R. W., Howie, A. J., Stewart, P. M. & Hewison, M. (2001) Extrarenal expression of 25-hydroxyvitamin d(3)-1 alpha-hydroxylase. J. Clin. Endocrinol. Metab 86: 888-894.
48. Somjen, D., Weisman, Y., Kohen, F., Gayer, B., Limor, R., Sharon, O., Jaccard, N., Knoll, E. & Stern, N. (2005) 25-hydroxyvitamin D3-1alpha-hydroxylase is expressed in human vascular smooth muscle cells and is upregulated by parathyroid hormone and estrogenic compounds. Circulation 111: 1666-1671.
49. Nieuwenhuijzen Kruseman, A. C., van der Klauv, M. M. & Pijpers, E. (2005) [Hormonal and metabolic causes of muscular weakness and the increased risk of fractures in elderly people]. Ned. Tijdschr. Geneeskd. 149: 1033-1037.
50. Bischoff-Ferrari, H. A., Borchers, M., Gudat, F., Durmuller, U., Stahelin, H. B. & Dick, W. (2004) Vitamin D receptor expression in human muscle tissue decreases with age. J. Bone Miner. Res. 19: 265-269.
51. Bischoff, H. A., Stahelin, H. B., Dick, W., Akos, R., Knecht, M., Salis, C., Nebiker, M., Theiler, R., Pfeifer, M. et al. (2003) Effects of vitamin D and calcium supplementation on falls: a randomized controlled trial. J. Bone Miner. Res. 18: 343-351.
52. Bischoff-Ferrari, H. A., Giovannucci, E., Willett, W. C., Dietrich, T. & wson-Hughes, B. (2006) Estimation of optimal serum concentrations of 25-hydroxyvitamin D for multiple health outcomes. Am. J. Clin. Nutr. 84: 18-28.
53. Wicherts, I. S., van Schoor, N. M., Boeke, A. J., Visser, M., Deeg, D. J., Smit, J., Knol, D. L. & Lips, P. (2007) Vitamin D status predicts physical performance and its decline in older persons. J. Clin. Endocrinol. Metab 92: 2058-2065.
54. Vieth, R., Bischoff-Ferrari, H., Boucher, B. J., wson-Hughes, B., Garland, C. F., Heaney, R. P., Holick, M. F., Hollis, B. W., Lamberg-Allardt, C. et al. (2007) The urgent need to recommend an intake of vitamin D that is effective. Am. J. Clin. Nutr. 85: 649-650.
55. Simpson, R. U., Thomas, G. A. & Arnold, A. J. (1985) Identification of 1,25-dihydroxyvitamin D3 receptors and activities in muscle. J. Biol. Chem. 260: 8882-8891.
56. Capiati, D., Benassati, S. & Boland, R. L. (2002) 1,25(OH)2-vitamin D3 induces translocation of the vitamin D receptor (VDR) to the plasma membrane in skeletal muscle cells. J. Cell Biochem. 86: 128-135.
57. Nemere, I., Dormanen, M. C., Hammond, M. W., Okamura, W. H. & Norman, A. W. (1994) Identification of a specific binding protein for 1 alpha,25-dihydroxyvitamin D3 in basal-lateral membranes of chick intestinal epithelium and relationship to transcaltachia. J. Biol. Chem. 269: 23750-23756.
58. Haddad, J. G., Jr. & Birge, S. J. (1971) 25-Hydroxycholecalciferol: specific binding by rachitic tissue extracts. Biochem. Biophys. Res. Commun. 45: 829-834.
59. Birge, S. J. & Haddad, J. G. (1975) 25-hydroxycholecalciferol stimulation of muscle metabolism. J. Clin. Invest 56: 1100-1107.
60. Haddad, J. G. & Birge, S. J. (1975) Widespread, specific binding of 25-hydroxycholecalciferol in rat tissues. J. Biol. Chem. 250: 299-303.
61. Boland, R. (1986) Role of vitamin D in skeletal muscle function. Endocr. Rev. 7: 434-448.
62. Zanello, S. B., Boland, R. L. & Norman, A. W. (1995) cDNA sequence identity of a vitamin D-dependent calcium-binding protein in the chick to calbindin D-9K. Endocrinology 136: 2784-2787.
63. Snijder, M. B., van Schoor, N. M., Pluijm, S. M., van Dam, R. M., Visser, M. & Lips, P. (2006) Vitamin D status in relation to one-year risk of recurrent falling in older men and women. J. Clin. Endocrinol. Metab 91: 2980-2985.
64. Sato, Y., Iwamoto, J., Kanoko, T. & Satoh, K. (2005) Low-dose vitamin D prevents muscular atrophy and reduces falls and hip fractures in women after stroke: a randomized controlled trial. Cerebrovasc. Dis. 20: 187-192.
65. Boland, R., Norman, A., Ritz, E. & Hasselbach, W. (1985) Presence of a 1,25-dihydroxy-vitamin D3 receptor in chick skeletal muscle myoblasts. Biochem. Biophys. Res. Commun. 128: 305-311.
66. Costa, E. M., Blau, H. M. & Feldman, D. (1986) 1,25-dihydroxyvitamin D3 receptors and hormonal responses in cloned human skeletal muscle cells. Endocrinology 119: 2214-2220.
67. Burne, T. H., McGrath, J. J., Eyles, D. W. & kay-Sim, A. (2005) Behavioural characterization of vitamin D receptor knockout mice. Behav. Brain Res. 157: 299-308.
68. DeLuca, H. F. (1988) The vitamin D story: a collaborative effort of basic science and clinical medicine. FASEB J. 2: 224-236.
69. Bischoff, H. A., Borchers, M., Gudat, F., Duermueller, U., Theiler, R., Stahelin, H. B. & Dick, W. (2001) In situ detection of 1,25-dihydroxyvitamin D3 receptor in human skeletal muscle tissue. Histochem. J. 33: 19-24.
70. Freedman, L. P. (1999) Transcriptional targets of the vitamin D3 receptor-mediating cell cycle arrest and differentiation. J. Nutr. 129: 581S-586S.
71. Boland, R., De Boland, A. R., Marinissen, M. J., Santillan, G., Vazquez, G. & Zanello, S. (1995) Avian muscle cells as targets for the secosteroid hormone 1,25-dihydroxy-vitamin D3. Mol. Cell Endocrinol. 114: 1-8.
72. De Boland, A. R. & Boland, R. (1985) In vitro cellular muscle calcium metabolism. Characterization of effects of 1,25-dihydroxy-vitamin D3 and 25-hydroxy-vitamin D3. Z. Naturforsch. [C.] 40: 102-108.

73. Morelli, S., Boland, R. & De Boland, A. R. (1996) 1,25(OH)2-vitamin D3 stimulation of phospholipases C and D in muscle cells involves extracellular calcium and a pertussis-sensitive G protein. Mol. Cell Endocrinol. 122: 207-211.
74. Vazquez, G., De Boland, A. R. & Boland, R. L. (1997) 1 alpha,25-(OH)2-vitamin D3 stimulates the adenylyl cyclase pathway in muscle cells by a GTP-dependent mechanism which presumably involves phosphorylation of G alpha i. Biochem. Biophys. Res. Commun. 234: 125-128.
75. Boland, R., De Boland, A. R., Buitrago, C., Morelli, S., Santillan, G., Vazquez, G., Capiati, D. & Baldi, C. (2002) Non-genomic stimulation of tyrosine phosphorylation cascades by 1,25(OH)(2)D(3) by VDR-dependent and -independent mechanisms in muscle cells. Steroids 67: 477-482.
76. Selles, J. & Boland, R. (1991) Rapid stimulation of calcium uptake and protein phosphorylation in isolated cardiac muscle by 1,25-dihydroxyvitamin D3. Mol. Cell Endocrinol. 77: 67-73.
77. Wu, Z., Woodring, P. J., Bhakta, K. S., Tamura, K., Wen, F., Feramisco, J. R., Karin, M., Wang, J. Y. & Puri, P. L. (2000) p38 and extracellular signal-regulated kinases regulate the myogenic program at multiple steps. Mol. Cell Biol. 20: 3951-3964.
78. Cornet, A., Baudet, C., Neveu, I., Baron-Van, E. A., Brachet, P. & Naveilhan, P. (1998) 1,25-Dihydroxyvitamin D3 regulates the expression of VDR and NGF gene in Schwann cells in vitro. J Neurosci. Res. 53: 742-746.
79. Sanchez, B., Relova, J. L., Gallego, R., Ben-Batalla, I. & Perez-Fernandez, R. (2009) 1,25-Dihydroxyvitamin D3 administration to 6-hydroxydopamine-lesioned rats increases glial cell line-derived neurotrophic factor and partially restores tyrosine hydroxylase expression in substantia nigra and striatum. J Neurosci. Res. 87: 723-732.
80. Baier, S., Johannsen, D., Abumrad, N. N., Rathmacher, J. A., Nissen, S. L. & Flakoll, P. J. (2009) Year-long changes in lean body mass in elderly men and women supplemented with a nutritional cocktail of β-hydroxy-β-methylbutyrate (HMB), arginine, and lysine. JPEN 33: 71-82.
81. Holick, M. F. (2007) Vitamin D deficiency. N. Engl. J. Med. 357: 266-281.
82. Heaney, R. P. (2008) Vitamin D in Health and Disease. Clin. J. Am. Soc. Nephrol. 3: 1535-1541.
83. Heaney, R. P. (2007) Vitamin D endocrine physiology. J. Bone Miner. Res. 22 Suppl 2: V25-V27.
84. Vieth, R., Bischoff-Ferrari, H., Boucher, B. J., wson-Hughes, B., Garland, C. F., Heaney, R. P., Holick, M. F., Hollis, B. W., Lamberg-Allardt, C. et al. (2007) The urgent need to recommend an intake of vitamin D that is effective. Am. J. Clin. Nutr. 85: 649-650.
85. Nieuwenhuijzen Kruseman, A. C., van der Klauv, M. M. & Pijpers, E. (2005) [Hormonal and metabolic causes of muscular weakness and the increased risk of fractures in elderly people]. Ned. Tijdschr. Geneeskd. 149: 1033-1037.
86. Holick, M. F. (2007) Vitamin D deficiency. N. Engl. J. Med. 357: 266-281.
87. Rogers, M. E., Sherwood, H. S., Rogers, N. L. & Bohlken, R. M. (2002) Effects of dumbbell and elastic band training on physical function in older inner-city African-American women. Women Health 36: 33-41.
88. Zion, A. S., De, M. R., Diamond, B. E. & Bloomfield, D. M. (2003) A home-based resistance-training program using elastic bands for elderly patients with orthostatic hypotension. Clin. Auton. Res. 13: 286-292.
89. Heislein, D. M., Harris, B. A. & Jette, A. M. (1994) A strength training program for postmenopausal women: a pilot study. Arch. Phys. Med. Rehabil. 75: 198-204.
90. Krebs, D. E., Jette, A. M. & Assmann, S. F. (1998) Moderate exercise improves gait stability in disabled elders. Arch. Phys. Med. Rehabil. 79: 1489-1495.
91. Smith, H. J., Wyke, S. M. & Tisdale, M. J. (2004) Mechanism of the attenuation of proteolysis-inducing factor stimulated protein degradation in muscle by beta-hydroxy-beta-methylbutyrate. Cancer Res. 64: 8731-8735.
92. Eley, H. L., Russell, S. T. & Tisdale, M. J. (2008) Attenuation of depression of muscle protein synthesis induced by lipopolysaccharide, tumor necrosis factor and angiotensin II by β-hydroxy-β-methylbutyrate. Am. J. Physiol Endocrinol. Metab 295: E1409-E1416.
93. Birge, S. J. & Haddad, J. G. (1975) 25-hydroxycholecalciferol stimulation of muscle metabolism. J. Clin. Invest 56: 1100-1107.
94. DeLuca, H. F. (1988) The vitamin D story: a collaborative effort of basic science and clinical medicine. FASEB J. 2: 224-236.
95. Menconi, M., Gonnella, P., Petkova, V., Lecker, S. & Hasselgren, P. O. (2008) Dexamethasone and corticosterone induce similar, but not identical, muscle wasting responses in cultured L6 and C2C12 myotubes. J Cell Biochem. 105: 353-364.
96. Fuller, J. C., Jr., Nissen, S. L. & Huiatt, T. W. (1993) Use of $^{18}$O-labelled leucine and phenylalanine to measure protein turnover in muscle cell cultures and possible futile cycling during aminoacylation. Biochem. J. 294: 427-433.
97. Xu, H., McCann, M., Zhang, Z., Posner, G. H., Bingham, V., El-Tanani, M. & Campbell, F. C. (2009) Vitamin D receptor modulates the neoplastic phenotype through antagonistic growth regulatory signals. Mol. Carcinog. 48: 758-772.
98. Gniadecki, R., Gajkowska, B. & Hansen, M. (1997) 1,25-dihydroxyvitamin D3 stimulates the assembly of adherens junctions in keratinocytes: involvement of protein kinase C. Endocrinology 138: 2241-2248.
99. Heaney, R., Davies, M., Chen, T., Holick, M., Barger-Lux, J. (2003) Human serum 25-hydroxycholecalciferol response to extended oral dosing with cholecalciferol. Am. J. Clin. Nutr. 77:204-210.

The invention claimed is:

1. A method for increasing strength of an elderly human in need thereof, the method comprising the steps of administering to said elderly human a composition comprising a combination of from about 0.5 g to about 30 g of β-hydroxy-β-methylbutyrate (HMB) and Vitamin D in an amount sufficient to raise blood levels of Vitamin D to at least 30 ng/ml, wherein upon said administration of said combination of HMB and Vitamin D to the elderly human, said strength is increased.

2. The method of claim 1, wherein said HMB is selected from the group consisting of its free acid form, its salt, its ester and its lactone.

3. The method of claim 1, wherein said HMB is a calcium salt.

4. The method of claim 1, wherein said Vitamin D is Vitamin $D_3$.

5. The method of claim 1, wherein said Vitamin D is Vitamin $D_2$.

6. The method of claim 1, wherein said composition is administered to said animal in an edible form.

7. The method of claim 1, wherein said composition is administered to said animal intravenously.

8. The method of claim 1, wherein the Vitamin D is greater than 500 IU and less than or equal to 4,000 IU.

9. A method for increasing strength of an elderly human in need thereof, the method comprising the steps of administering to said elderly human a composition comprising a combination of from about 0.5 g to about 30 g of β-hydroxy-β-methylbutyrate (HMB) and of from greater than 500 IU to about 4,000 IU of Vitamin D, wherein upon said administration of said synergistic combination of HMB and Vitamin D to the animal, said strength is increased.

10. The method of claim 9, wherein said HMB is selected from the group consisting of its free acid form, its salt, its ester and its lactone.

11. The method of claim 9, wherein said HMB is a calcium salt.

12. The method of claim 9, wherein said Vitamin D is Vitamin $D_3$.

13. The method of claim 9, wherein said composition is administered to said animal in an edible form.

14. A composition comprising a combination of from about 0.5 g to about 30 g of β-hydroxy-β-methylbutyrate (HMB) and from greater than 500 IU to about 4,000 IU of Vitamin D, wherein administration of the composition to an elderly human in need thereof increases the strength of the elderly human.

15. The composition of claim 14, wherein said HMB is a calcium salt.

16. The composition of claim 14, wherein said Vitamin D is Vitamin $D_3$.

17. The composition of claim 14, wherein the composition is a foodstuff.

18. The composition of claim 14, wherein the composition is a liquid.

19. The composition of claim 18, wherein the composition further comprises amino acids.

* * * * *